United States Patent
Uchiyama et al.

(10) Patent No.: US 8,790,248 B2
(45) Date of Patent: Jul. 29, 2014

(54) INDWELLING APPARATUS FOR BODY CAVITY INTRODUCING DEVICE AND BODY CAVITY INTRODUCING DEVICE PLACING SYSTEM

(75) Inventors: Akio Uchiyama, Kanagawa (JP); Hironobu Takizawa, Tokyo (JP); Shinsuke Tanaka, Tokyo (JP); Katsumi Hirakawa, Kanagawa (JP); Takeshi Yokoi, Tokyo (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 1285 days.

(21) Appl. No.: 11/884,669

(22) PCT Filed: Jul. 20, 2006

(86) PCT No.: PCT/JP2006/314418
§ 371 (c)(1),
(2), (4) Date: Aug. 17, 2007

(87) PCT Pub. No.: WO2007/010997
PCT Pub. Date: Jan. 25, 2007

(65) Prior Publication Data
US 2008/0167523 A1    Jul. 10, 2008

(30) Foreign Application Priority Data

Jul. 20, 2005 (JP) ................................. 2005-210633
Sep. 29, 2005 (JP) ................................. 2005-284627

(51) Int. Cl.
*A61B 1/00*    (2006.01)
(52) U.S. Cl.
USPC ........................... 600/118; 600/117; 600/136

(58) Field of Classification Search
USPC ......... 600/101, 102, 104, 109, 114–118, 120, 600/136
See application file for complete search history.

(56) References Cited

U.S. PATENT DOCUMENTS 7,083,579 B2 *   8/2006   Yokoi et al. .................... 600/593
2003/0139647 A1 *  7/2003   Raz et al. ....................... 600/104
(Continued)

FOREIGN PATENT DOCUMENTS

JP        6-114036         4/1994
JP        7-289504 A      11/1995
(Continued)

OTHER PUBLICATIONS

Japanese Office Action with translation dated Feb. 28, 2011 issued in JP2005-210633.

(Continued)

*Primary Examiner* — Anhtuan T Nguyen
*Assistant Examiner* — Rynae Boler
(74) *Attorney, Agent, or Firm* — Scully, Scott, Murphy & Presser, P.C.

(57) ABSTRACT

An indwelling apparatus (5) for holding a capsule endoscope (3) is arranged with a control device (57) including an optical sensor (73), a control board (66) configuring a controller and a reset circuit, a driver board (68) configuring an electromagnet driver, and an electromagnet (70), where when the optical sensor (73) detects the light, the controller performs the drive control of the electromagnet (70) at every constant time interval to turn ON the reed switch (14) and supply power to the capsule endoscope (3) thereby operating the capsule endoscope (3) only when observation is necessary, and thus the battery drain of the capsule endoscope is reduced.

6 Claims, 26 Drawing Sheets

(56) References Cited

U.S. PATENT DOCUMENTS

| | | | | |
|---|---|---|---|---|
| 2003/0208156 A1* | 11/2003 | Pham et al. | .................... | 604/113 |
| 2004/0133076 A1 | 7/2004 | Kobayashi et al. | | |
| 2004/0162469 A1* | 8/2004 | Imran | ........................... | 600/310 |
| 2004/0176664 A1* | 9/2004 | Iddan | ........................... | 600/160 |
| 2004/0181155 A1 | 9/2004 | Glukhovsky | | |
| 2004/0225184 A1* | 11/2004 | Shimizu et al. | ............... | 600/112 |
| 2004/0242962 A1 | 12/2004 | Uchiyama | | |
| 2004/0267095 A1 | 12/2004 | Miyake et al. | | |
| 2005/0020880 A1 | 1/2005 | Miyake et al. | | |
| 2005/0054897 A1* | 3/2005 | Hashimoto et al. | ........... | 600/118 |
| 2005/0124875 A1* | 6/2005 | Kawano et al. | ............... | 600/407 |
| 2005/0165272 A1* | 7/2005 | Okada et al. | .................. | 600/114 |
| 2005/0272974 A1* | 12/2005 | Iddan | ........................... | 600/106 |
| 2006/0167339 A1 | 7/2006 | Gilad et al. | | |
| 2006/0189846 A1* | 8/2006 | Huang et al. | .................. | 600/160 |
| 2007/0161851 A1* | 7/2007 | Takizawa et al. | ............. | 600/102 |

FOREIGN PATENT DOCUMENTS

| | | |
|---|---|---|
| JP | 2000-342522 A | 12/2000 |
| JP | 2003-093332 | 4/2003 |
| JP | 2003-135388 | 5/2003 |
| JP | 2004-000440 | 1/2004 |
| JP | 2004-350963 | 12/2004 |
| JP | 2005-13359 | 1/2005 |
| JP | 2005-021651 | 1/2005 |
| JP | 2005-073884 | 3/2005 |
| JP | 2005-073934 | 3/2005 |
| JP | 2005-073934 A | 3/2005 |
| JP | 2005-074031 | 3/2005 |
| JP | 2005-185567 | 7/2005 |
| WO | WO 01/35813 | 5/2001 |
| WO | WO 2004/054430 A3 | 7/2004 |
| WO | WO 2005/062717 A2 | 7/2005 |

OTHER PUBLICATIONS

European Search Report dated Mar. 28, 2012 from corresponding European Patent Application No. EP 06 78 1373.3.

Japanese Office Action dated Oct. 30, 2012 from corresponding Japanese Patent Application No. 2011-192089, together with an English language translation.

English language abstract only of Japanese Patent Application Publication No. JP 2004-350963 A dated Dec. 16, 2004.

English Language Abstract of Japanese Patent Application Laid-Open No. JP 2004-350963 published Dec. 16, 2004.

English Language Abstract of Japanese Patent Application Laid-Open No. JP 2004-357933 published Dec. 24, 2004.

* cited by examiner

INDWELLING APPARATUS FOR BODY CAVITY INTRODUCING DEVICE AND BODY CAVITY INTRODUCING DEVICE PLACING SYSTEM

TECHNICAL FIELD

The present invention relates to an indwelling apparatus for body cavity introducing device and a body cavity introducing device placing system for placing a body cavity introducing device, for example, a capsule endoscope of swallow type introduced into the body cavity.

BACKGROUND ART

A capsule endoscope equipped with an imaging function and a wireless function has recently appeared in the field of endoscopes. This capsule endoscope is configured so as to peristaltically move inside (body cavity) the organs such as stomach, small intestine and the like during the observation period from after being swallowed by a subject for observation (examination) until naturally excreted from the body (human body) of the subject, and to sequentially perform imaging using the imaging function.

During the observation period of the movement inside the organs, the image data imaged in the body cavity by the capsule endoscope are sequentially transmitted to an external device arranged exterior to the subject by means of wireless function such as wireless communication, and stored in a memory arranged in the external device. If the subject carries the external device having the wireless function and the memory function, the subject can move around without suffering from inconvenience during the observation period from after swallowing the capsule endoscope until excreted. After observation, doctors, nurses etc. are able to display the image of the body cavity on a display unit such as a display based on the image data stored in the memory of the external device, and make a diagnosis.

This type of capsule endoscope includes a swallow type as disclosed in Patent Document 1, for example, of interiorly arranging a reed switch that is turned ON/OFF by the external magnetic field to control the drive of the electric load for executing the imaging function, the wireless function and the like in the capsule endoscope, and being accommodated in a package including a permanent magnet for supplying such external magnetic field is proposed. That is, the reed switch arranged in the capsule endoscope has a configuration of maintaining an OFF state in the environment where a magnetic field of greater than or equal to a constant strength is applied, and being turned ON when the strength of the external magnetic field decreases. Thus, the electric load is not driven while being accommodated in the package. When the capsule endoscope is taken out from the package in time of swallowing, the capsule endoscope will no longer be influenced by the magnetic force as it is isolated from the permanent magnet, whereby the drive of the electric load starts. According to such configuration, the drive of the electric load is prevented while being accommodated in the package, and the imaging of the image by means of the imaging function as well as the transmission of the image signal by means of the wireless function of the capsule endoscope are performed after being taken out from the package.

Patent Document 1: International Publication No. 01/35813 Pamphlet

DISCLOSURE OF INVENTION

Problem to be Solved by the Invention

Recently, however, it is desired to place the capsule endoscope in the body cavity such as the stomach, small intestine and the like in place of the usual endoscope with a long insertion part to be inserted into the subject, and perform observation of the affected site or post-operation, for example, observation of bleeding and the like over a long period of time. That is, there is an increasing demand for the patient to swallow the capsule endoscope, and continuously perform the observation of the same site at every constant interval in order to alleviate the patient's pain of inserting the usual endoscope at every constant interval of the observation, reduce the cost of hygienics of the endoscope at hospitals, etc. The imaging of about eight hours at an imaging rate of two comas per one second is possible, for example, with the current capsule endoscope, but the battery in the capsule endoscope is sometimes drained if the capsule endoscope is placed by the indwelling apparatus in the body cavity for a long time.

It is an object of the present invention to, in view of the above problems, provide an indwelling apparatus for body cavity introducing device and a body cavity introducing device placing system that reduces the battery drain of the capsule endoscope.

Means for Solving Problem

An indwelling apparatus for body cavity introducing device according to one aspect of the present invention includes a holding unit for holding a body cavity introducing device for acquiring information of the inside of the body cavity; a body cavity tissue binding unit for fixing to the tissue in the body cavity; and a body cavity introducing device control unit for controlling power consuming operation of the body cavity introducing device.

In the indwelling apparatus for body cavity introducing device, the body cavity introducing device control unit may control a power switch of the body cavity introducing device.

In the indwelling apparatus for body cavity introducing device, the body cavity introducing device control unit may include a first interface for receiving an input from an external device, and changes the controlling state of the body cavity introducing device with the input to the first interface.

In the indwelling apparatus for body cavity introducing device, the body cavity introducing device control unit may include a second interface for transmitting a signal for controlling the operation of the body cavity introducing device to the body cavity introducing device.

An indwelling apparatus for body cavity introducing device according to another aspect of the invention includes, an indwelling apparatus main body including a holding unit for attaching a body cavity introducing device; an attachment for attaching the indwelling apparatus in a living body; and a body cavity introducing device control unit for issuing an operation start command and an operation stop command to the body cavity introducing device attached to the holding unit.

In the indwelling apparatus for body cavity introducing device, the body cavity introducing control unit may issue the operation start command and the operation stop command upon receiving a wireless signal.

In the indwelling apparatus for body cavity introducing device, the body cavity introducing device control unit may repeatedly output the operation start command and the operation stop command at a predetermined time interval.

A body cavity introducing device placing system according to still another aspect of the invention includes a body cavity introducing device including an information acquiring unit for acquiring information of the inside of the body cavity, a transmitting unit for transmitting the information acquired in the information acquiring unit to an external device, an internal control unit for controlling the information acquiring unit and the transmitting unit, a power supplying unit for supplying power to each unit, a power switch for controlling the power supply from the power supplying unit to each unit; and an indwelling apparatus for body cavity introducing device including a holding unit for holding the body cavity introducing device, a body cavity tissue binding unit for fixing to the tissue in the body cavity, and a body cavity introducing device control unit for controlling power consuming operation of the body cavity introducing device.

Effect of the Invention

According to the indwelling apparatus for body cavity introducing device and the body cavity introducing device placing system of the present invention, power is supplied to a constituting site of the body cavity introducing device (capsule endoscope) only when observation is required by arranging a body cavity introducing device control unit for controlling the power consuming operation of the body cavity introducing device in the indwelling apparatus for body cavity introducing device, thereby reducing the battery drain of the capsule endoscope.

EXPLANATIONS OF LETTERS OR NUMERALS

Figure 1:
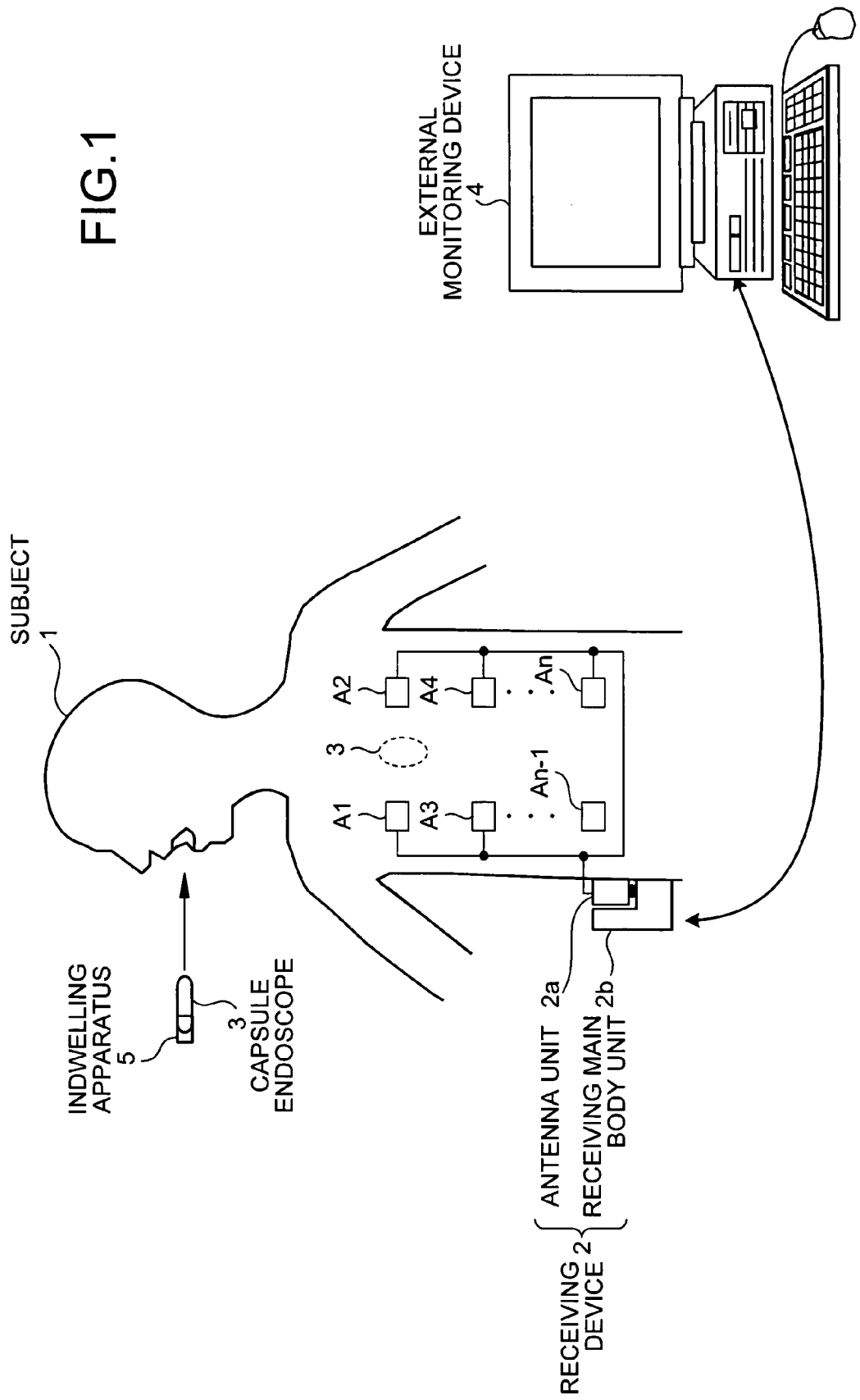
FIG. 1 is a frame format view showing an entire configuration of a wireless subject information acquiring system, which is a preferred embodiment of an indwelling apparatus for body cavity introducing device according to the present invention.

1 Subject
2 Receiving device
2a Wireless unit
2b Receiving main body unit
3 capsule endoscope
4 External monitoring device
5 Indwelling apparatus
7 Clip
8 Endoscope
9 Hood
10 Image sensor
11, 82 LED
12 CCD
13 Optical system device
14 Reed switch
15 Power supply unit
16 Capsule shaped housing
17 Wireless unit
18, 87 RF transmission device
19 Antenna
20 Imaging board
21 Illumination board
22 Signal processing and controlling unit
23 Wireless board
24, 72 Battery
25 LED driving circuit
26 CCD driving circuit
27 System control circuit
28 Electrode board
29, 73 Optical sensor
30 Receiving module
31 Battery
32 Power switch
33 External device controller
34 Power supplying coil
35 Coil driver
36 Input switch
37 Memory
38, 52 Display device
39, 50 Wireless device
40 Receiving housing
51, 67, 75, 86 Controller
55 Holding part (attachment)
56 Binding part
57 Control device
58 Bottom
59 Tube body
60 Projecting member (hook part)
61, 129 Hole
62 Power receiving coil
63 Power supply board
64 Rectifier
65 Power supply device
66 Control board
68 Driver board
69 Electromagnet driver
70 Magnetic body (electromagnet)
70a, 70b End
71, 74 Reset circuit
76 Motor driver
77 Permanent magnet
77c, 77d Bias magnet
78 Pulley
79 Rope
80 Shaft
81 Spring
83 LED driver
84 RF Receiving device
85, 88 Antenna
128 Button switch (mechanical switch)
140, 141, 162, 163 Electrode
142 Electrometer
157 Pin
164 Resistor
165 Permanent magnet
A1 to An Receiving antenna
K Coil
M Motor

MODE(S) FOR CARRYING OUT THE INVENTION

Exemplary embodiments of an indwelling apparatus for body cavity introducing device and a body cavity introducing device placing system according to the present invention will now be described in detail based on the drawings of FIGS. 1 to 25. The present invention is not limited to such embodiments, and various modifications are possible without departing from the scope of the invention.

First Embodiment

FIG. 1 is a frame format view showing an entire configuration of a wireless subject information acquiring system, which is a preferred embodiment of the indwelling apparatus for body cavity introducing device according to the present invention. The subject information acquiring system uses a capsule endoscope as one example of the subject introducing unit. As shown in FIG. 1, the wireless subject information acquiring system includes a capsule endoscope 3, serving as a body cavity introducing device, introduced into a subject 1 to image a body cavity image and perform data transmission of picture signal and the like to a receiving device 2; an indwelling apparatus for body cavity introducing device (hereinafter simply referred to as "indwelling apparatus") 5 for controlling the operation of the capsule endoscope 3; and the receiving device 2 serving as an external device for receiving the body cavity image data wirelessly transmitted from the capsule endoscope 3. The wireless subject information acquiring system includes an external monitoring system 4 for monitoring the body cavity image based on the picture signal received by the receiving device 2, where data exchange between the receiving device 2 and the external monitoring device 4 is performed by connecting the receiving device 2 and the external monitoring device 4 in a wired or wireless manner.

The receiving device 2 includes a wireless unit 2a with a plurality of receiving antennae A1 to An attached to the external surface of the subject 1, and a receiving main body unit 2b for performing processes and the like of the wireless signal received via the plurality of receiving antennae A1 to An, which units are removably connected by way of a connector and the like. Each of the receiving antennae A1 to An is attached to a jacket worn by the subject 1, for example, and the subject 1 may carry the receiving antennae A1 to An by wearing the jacket. In this case, the receiving antennae A1 to An may be removable with respect to the jacket. The number of the receiving antenna may be one when placing the capsule endoscope, and one antenna may be attached to a position where reception of the transmitted signal from the capsule endoscope is satisfactorily performed after placing.

Figure 2:
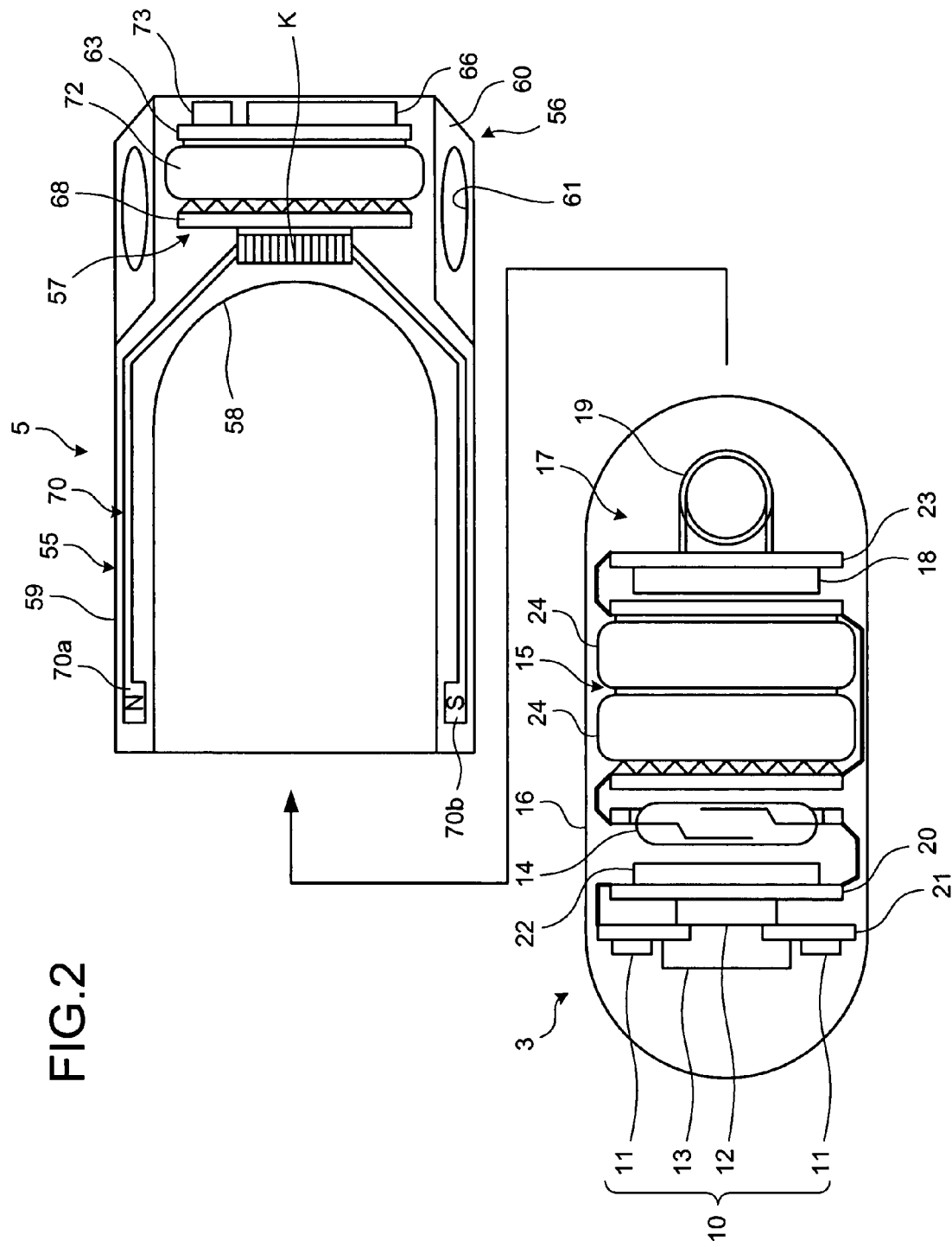
FIG. 2 is a cross sectional view showing an inner configuration of a body cavity introducing device placing system in which a capsule endoscope and an indwelling apparatus according to a first embodiment shown in FIG. 1 are separated.
Figure 3:
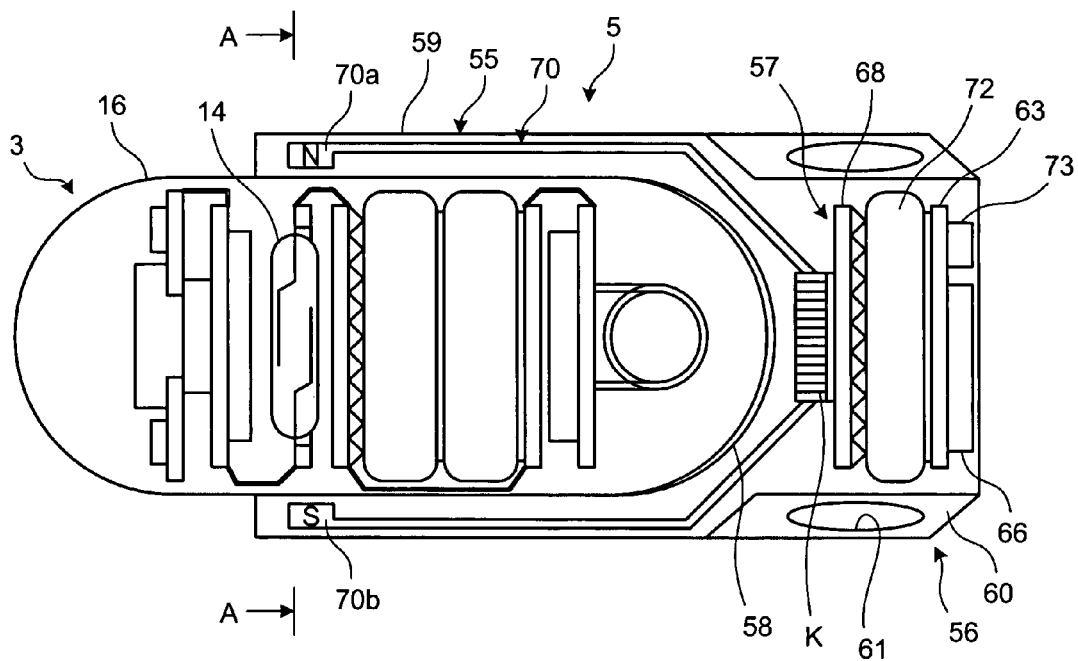
FIG. 3 is a cross sectional view showing an inner configuration of the body cavity introducing device placing system in which the capsule endoscope and the indwelling apparatus according to the first embodiment are coupled.

The capsule endoscope 3 and the indwelling apparatus 5 configure the body cavity introducing device placing system, where the capsule endoscope 3 is swallowed into the subject 1 while being held in the indwelling apparatus 5. The capsule endoscope 3 will now be described using FIGS. 2 and 3. FIG. 2 is a cross sectional view showing an inner configuration of the body cavity introducing device placing system in which the capsule endoscope 3 and the indwelling apparatus 5 according to the first embodiment shown in FIG. 1 are separated, and FIG. 3 is a cross sectional view showing an inner configuration of the body cavity introducing device placing system in which the capsule endoscope 3 and the indwelling apparatus 5 are coupled. The capsule endoscope 3 includes an image sensor 10 serving as an information acquiring unit including an LED 11 etc. serving as an illuminating unit for illuminating the inside of the body cavity of the subject 1, a CCD 12 etc. serving as an imaging unit for imaging the image of the inside the body cavity, and an optical system device 13 serving an optical unit for imaging the image of the inside of the body cavity to an imaging position of the CCD 12; and a wireless unit 17 including a RF transmission device 18 serving as a transmitting unit for transmitting the image data imaged at the CCD 12 and an antenna 19, where the image sensor 10 and the wireless unit 17 are connected to a power supply unit 15 serving as a power supplying unit for supplying power thereto via a reed switch 14 serving as a power switch, and are arranged in a capsule shaped housing 16. The reed switch 14 may have a circuit configuration configuring a trigger switch for outputting a control signal for turning ON/OFF the power supply control circuit (not shown).

The capsule shaped housing 16 has a transparent hemispherical dome shaped front cover housing for covering the image sensor 10, the wireless unit 17 and the like; and a cylindrical core housing that engages the front cover housing, that is arranged with the image sensor 10 and the wireless unit 17 with the power supply unit 15 interposed in between in the inside maintained in a water tight manner, and that is formed to a size capable of being swallowed from the mouth of the subject 1. The core housing is formed by a colored material that does not transmit visible light.

The CCD 12, arranged on an imaging board 20, images the range illuminated by the illumination light from the LED 11; and the optical system device 13 is made up of imaging lens for imaging the subject image to the CCD 12. The LED 11 is mounted on an illumination board 21 and arranged at four locations thereof near the top, bottom, left and right with the optical axis of the imaging lens as the center. Furthermore, in the image sensor 10, a signal processing and controlling unit 22 for processing and controlling each section is mounted on the back surface side of the imaging board 20 as an internal control unit for controlling the image sensor 10 and the RF transmission device 18. The imaging board 20, the illumination board 21, the signal processing and controlling unit 22, and the wireless board 23 are electrically connected by an appropriate flexible board.

The power supply unit 15 is configured by a button type battery 24, 24 having a diameter that substantially matches the inner diameter of the core housing and the like. The battery 24, 24 may be silver oxide cell, a rechargeable battery, power generating cell and so on. The RF transmission device 18 is arranged on the back surface side of the wireless board 23, and the antenna 19 is mounted on the wireless board 23.

Figure 5:
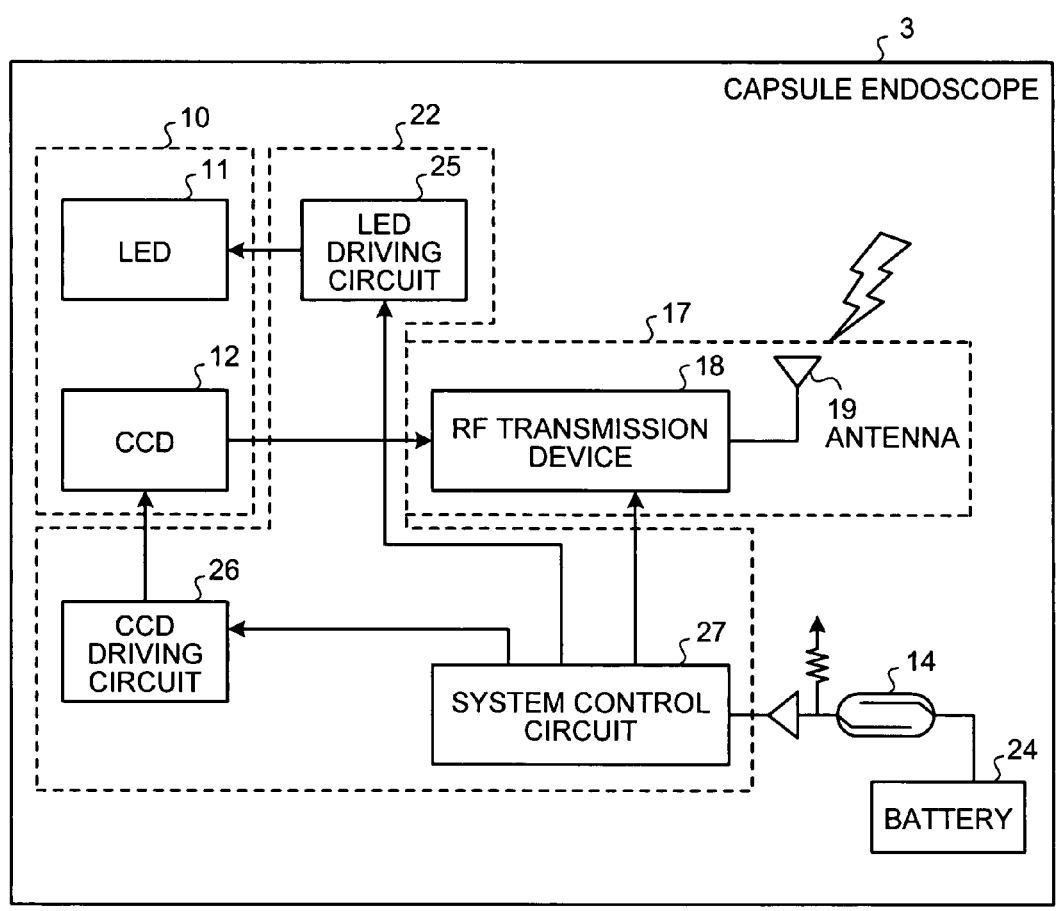
FIG. 5 is a block diagram showing one example of a circuit configuration of the capsule endoscope shown in FIG. 2.

The circuit configuration of the capsule endoscope 3 will now be described using FIG. 5. FIG. 5 is a block diagram showing one example of a circuit configuration of the capsule endoscope 3 shown in FIG. 2. The capsule endoscope 3 includes LED 11 and CCD 12 as the image sensor 10; an LED driving circuit 25 for controlling the driving state of the LED 11, a CCD driving circuit 26 for controlling the driving state of the CCD 12, and a system control circuit 27 serving as a control unit for controlling the operation of the LED driving circuit 25, the CCD driving circuit 26 and the RF transmission device 18 as the signal processing and controlling unit 22; and includes the RF transmission device 18 and the antenna 19 as the wireless unit 17.

The capsule endoscope 3 operates so as to acquire by means of the CCD 12 the image data of the site of the subject irradiated by the LED 11 while the capsule endoscope 3 is introduced in the subject 1 by arranging the system control circuit 27. The acquired image data is further converted to the RF signal by the RF transmission device 18 and transmitted to the outside of the subject 1 via the antenna 19. Furthermore, the capsule endoscope 3 includes the battery 24 for supplying power to the system control circuit 27 via the reed switch 14, and the system control circuit 27 has a function of distributing the driving power supplied form the battery 24 to other components (LED driving circuit 25, CCD driving circuit 26, RF transmission device 18).

The reed switch 14 is turned ON when magnetized by the influence of the magnetic field of the magnet applied from the outside and the contacting points contact, thereby allowing the supply of driving power from the battery 24 to the system control circuit 27. The reed switch 14 is configured so as to be turned OFF when magnetized by the influence of the magnetic field of the magnet applied from the outside and the contacting points do not contact and to be turned ON when the influence of the magnetic field is diminished and the contacting points contact, thereby allowing the supply of driving power from the battery 24 to the system control circuit 27.

Figure 6:
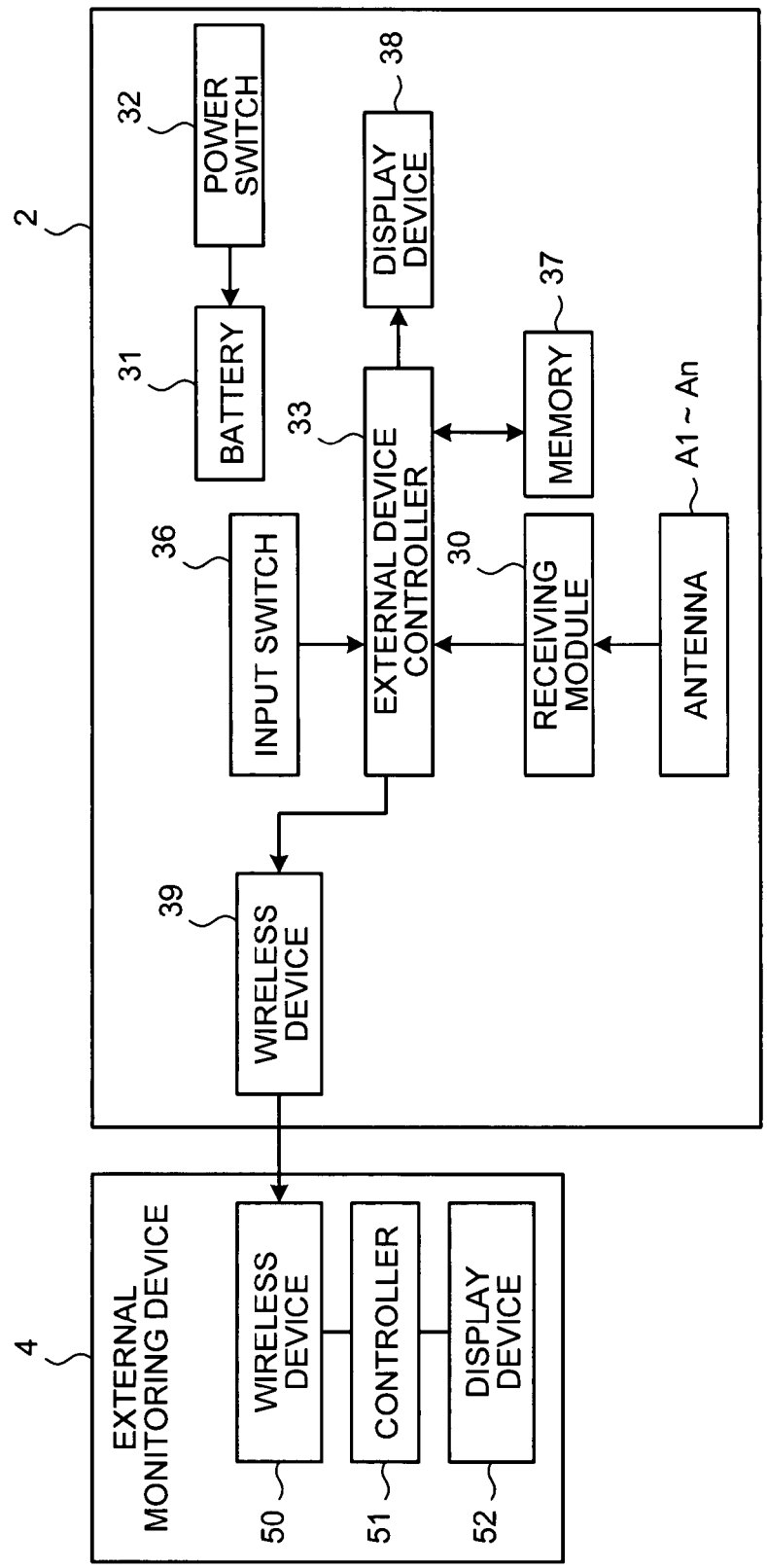
FIG. 6 is a block diagram showing a circuit configuration of a receiving device and an external monitoring device according to the first embodiment shown in FIG. 1.

The circuit configuration of the receiving device 2 will now be described using FIG. 6. FIG. 6 is a block diagram showing a circuit configuration of the receiving device 2 and the external monitoring device 4 according to the first embodiment shown in FIG. 1. In the first embodiment, the circuit configuration of the wireless unit 2a and the receiving main body unit 2b is shown as one block in FIG. 5. The receiving device 2 includes a receiving module 30 and antennae A1 to An. The receiving module 30 functions to amplify and demodulate the signal of the electric wave captured at the antennae A1 to An, and is configured by the wireless unit 2a portion.

The receiving device 2 is configured by a battery 31, a power switch 32, an external device controller 33, an input switch 36, a memory 37, a display device 38 made up of small liquid crystal display etc., and a wireless device 39, and is configured by the receiving main body unit 2b portion. The power switch 32 is turned ON/OFF so as to allow the supply of power from the battery 31 to each component. The external device controller 33 performs image processing of the image information on the body cavity received by the receiving module 30 and stores the same in the memory 37, performs display control so as to display the image information on the display device 38, and performs communication control so as to transmit the same from the wireless device 39 to the external monitoring device 4.

The external monitoring device 4 displays body cavity image and the like imaged by the capsule endoscope 3, and has a configuration of a work station and the like in which the controller 51 displays the image on the display device 52 based on the data received by the wireless device 50, as shown in the block diagram of FIG. 6. Specifically, the external monitoring device 4 may have a configuration of directly displaying the image by CRT display, liquid crystal display and the like, or may have a configuration of outputting the image to other medium such as a printer.

The indwelling apparatus 5 will now be described using FIGS. 2 and 3. FIG. 2 is a cross sectional view showing an inner configuration of the body cavity introducing device placing system in which the capsule endoscope and the indwelling apparatus according to the first embodiment shown in FIG. 2 are separated, and FIG. 3 is a cross sectional view showing an inner configuration of the body cavity introducing device placing system in which the capsule endoscope and the indwelling apparatus according to the first embodiment are coupled. In the figures, the indwelling apparatus 5 includes a holding part 55 serving as a holding unit for interiorly holding the capsule endoscope 3, a binding unit 56 serving as a body cavity tissue binding unit for binding to the body cavity tissue, and a control device 57 serving as a body cavity introducing device control unit for controlling the operation of the capsule endoscope 3. The holding part 55 is made of a cylindrical tube body 59 having a bottomed bottom 58 at one end, where the inner diameter of the tube body 59 is configured to be substantially the same as the outer diameter of the core housing of the capsule endoscope 3, and the bottom 58 is configured to be substantially the same as the outer shape of the front cover housing of the capsule endoscope 3. Thus, the capsule endoscope 3 is accommodated in the tube body 59 of the holding part 55 in a holdable manner and configures the body cavity introducing device placing system with the indwelling apparatus 5, as shown in FIG. 3.

The binding part 56 is configured by two ear shaped projecting members 60 projecting to the outer peripheral surface of the tube body 59, and a circular hole 61 passing from the front to the back is formed in the projecting member 60. A clip is passed through the hole 61 of the binding part 56 and clipped to the tissue of the body cavity to allow the capsule endoscope 3 to be placed in the body cavity over a long period of time.

The control device 57 includes an optical sensor 73 serving as a light detecting unit arranged on the power supply board 63, and a control board 66 configuring a reset circuit 74 and the controller 75, all of which configure the first interface. The control device 57 includes a driver board 68 arranged under the power supply board 63 and configuring an electromagnetic driver 69, and a magnetic body 70, both of which configure the second interface (electromagnet).

The magnetic body 70 is configured into a two leg shape with magnetic body ends 70a, 70b, and is formed so that both ends 70a, 70b are arranged at the same position in the reed switch 14 when the capsule endoscope 3 is held in the indwelling apparatus 5. Around the magnetic body 70 is wound a coil K, and the magnetic body 70 is magnetized by flowing current to the coil K from the electromagnetic driver 69, and, for example, the magnetic pole N is generated at end 70a and the magnetic pole S is generated at end 70b, thereby functioning as an electromagnet. When the magnetic body 70 functions as the electromagnet, the magnetic circuit is formed by way of the electrodes of the reed switch 14. When the magnetic circuit is formed, the reed switch 14 is magnetized and magnetic attraction is produced between the contacting points, whereby the contacting points contact thereby obtaining the ON state. The optical sensor 73 is arranged at the distal end on the bottom 58 side of the holding part 55, and has a function of a switch of detecting the externally irradiated light and allowing the supply of power from the battery 72.

Figure 7:
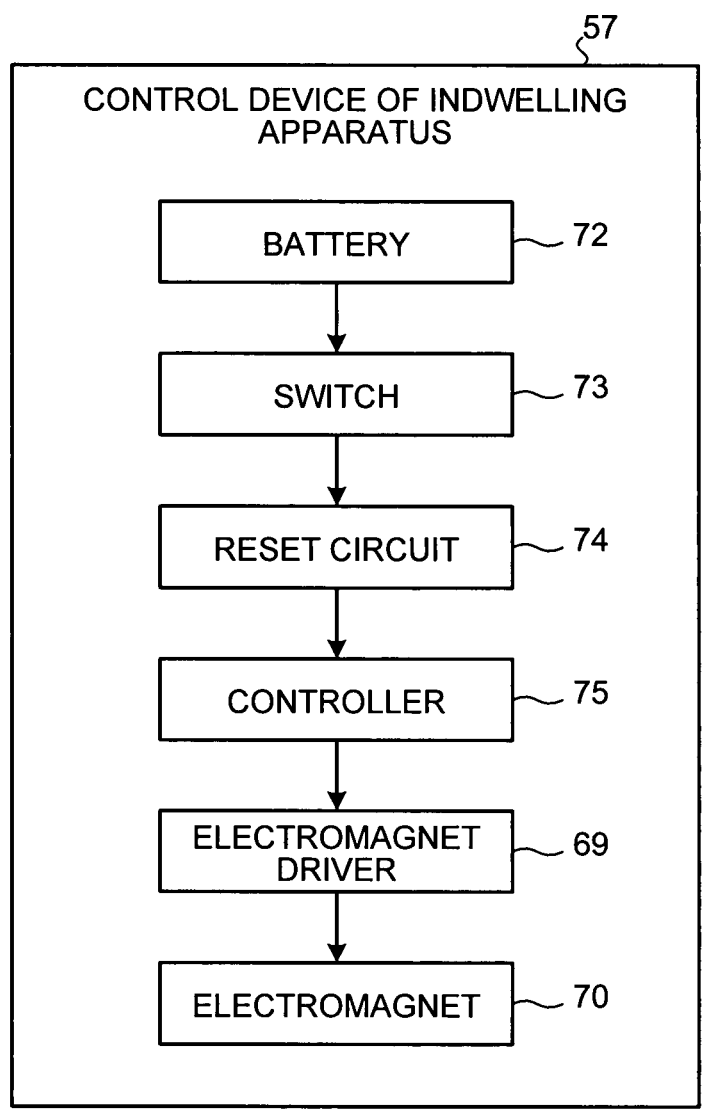
FIG. 7 is a block diagram showing a circuit configuration of the control device of the indwelling apparatus according to the first embodiment shown in FIG. 1.

The inner configuration of the control device 57 of the indwelling apparatus 5 will now be described using FIG. 7. FIG. 7 is a block diagram showing a circuit configuration of the control device 57 of the indwelling apparatus 5 according to the first embodiment shown in FIG. 2. With reference to FIG. 7, before the capsule endoscope 3 and the indwelling apparatus 5 are swallowed by the subject 1, the control device 57 has the optical sensor (switch) 73 irradiated with the light from the outside in advance so as to be activated and then swallowed by the subject 1. When power is supplied from the battery 72, the system reset is performed by the reset circuit 74, and thereafter, the controller 75 operation controls the electromagnet driver 69 at every constant time interval to flow current to the coil K from the electromagnet driver 69 thereby magnetizing the magnetic body 70. Due to magnetization of the magnetic body 70, a magnetic circuit is formed between the reed switch 14 and the magnetic body 70 and the magnetic field is generated, whereby the contacting points of the reed switch 14 contact and the power is supplied from the power supply unit 15 to each section of the capsule endoscope 3.

In the first embodiment, the indwelling apparatus 5 must be activated in advance before being swallowed since the capsule endoscope 3 cannot be operation controlled after the body cavity introducing device placing system is swallowed by the subject 1, and after being swallowed, the indwelling apparatus 5 operation controls the capsule endoscope 3 at every constant time to perform imaging of the body cavity image by means of the image sensor and transmission of the image data by means of the wireless unit. In other words, in the present embodiment, a command for performing the operation control of the capsule endoscope at a constant time interval, that is, a command for operation controlling the electromagnet driver 69 at a constant time interval is programmed in the controller 75, and a command control of repeating the above operation control at a constant time interval of once every 30 minutes or one hour etc. is performed.

In the first embodiment, when the optical sensor having a switch function detects the light, the controller performs the drive control of the electromagnet at every constant time interval to turn ON the reed switch of the capsule endoscope and allow the supply of power, thereby operating the image sensor and the wireless unit to perform the imaging of the body cavity and the transmission of the imaged image, and thus the electromagnet can be driven to turn ON the reed switch when observation is necessary, and the electromagnet can be stopped to turn OFF the reed switch when observation is not necessary, that is, the time interval in which the image sensor and the wireless unit operate can be extended. The battery drain of the capsule endoscope is thereby reduced. In other words, the control device 57 controls the power supply consuming operation of the capsule endoscope. Thus, in the embodiment, the photographing time interval is extended, and reduction of unnecessary image data and long time drive of the capsule endoscope are achieved.

The configuration of the reed switch may be such that the OFF state is obtained when magnetic field is applied and the contacting points contact, and the ON state is obtained when the magnetic field is not applied and contacting points separate. In such configuration, the battery drain of the capsule endoscope is reduced, similar to the first embodiment, by driving the electromagnet of the indwelling apparatus to apply the magnetic field and turn OFF the reed switch at the initial state, and operation controlling the electromagnet so that the magnetic field is not applied to the reed switch and the reed switch is turned ON when necessary. The reed switch performs the ON/OFF operation with a predetermined pattern, in which case, the effects similar to the first embodiment are obtained by operation controlling the electromagnet according to the pattern.

Figure 4:
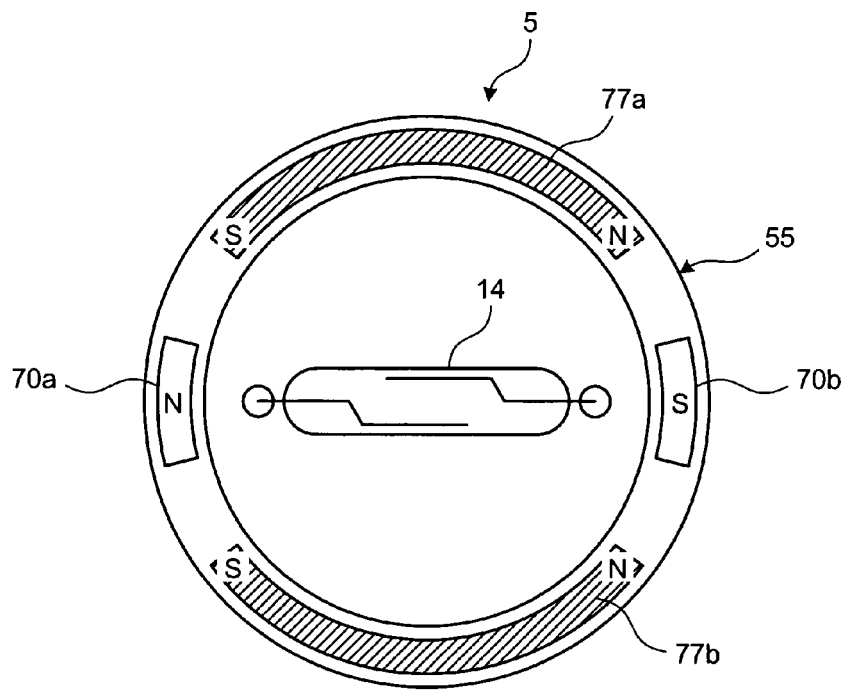
FIG. 4 is a cross sectional view showing a modification of a cross section taken along line A-A of FIG. 3.

FIG. 4 is a cross sectional view showing a modification of the cross section taken along line A-A of FIG. 3. When bias magnets 77a, 77b are arranged on the inner surface of the magnetic body ends 70a, 70b of the holding part 55 of the indwelling apparatus 5 as in FIG. 3, and the electromagnet is not driven, the contacting points of the reed switch 14 contact each other to be in the OFF state, and when the electromagnet is driven, the magnetic field passing through the reed switch 14 weakens and the contacting points of the reed switch 14 separate to be in the ON state.

According to the configuring of the modification, the power consumption of the indwelling apparatus is suppressed low since current needs to be flowed to the electromagnet only when the capsule endoscope is desired to be operated. The reed switch 14 does not directly control the power supply, but is configured as a switch for generating the ON/OFF signal to the separately arranged power supply control circuit (IC).

Second Embodiment

The indwelling apparatus for body cavity introducing device according to a second embodiment will now be described. The capsule endoscope 3 shown in FIGS. 8 and 9, and the external monitoring device 4 shown in FIG. 10 have the same configuration as the first embodiment, and thus the description thereof will not be repeated.

The receiving device 2 includes a power supplying coil 34 and a coil driver 35 for driving the power supplying coil 34, in addition to the configuration of the first embodiment. The external device controller 33 performs the functions similar to the first embodiment, and also operation controls the coil driver 35 to supply power to the power supplying coil 34 and generate the magnetic field when the input switch 36 is turned ON.

Figure 11:
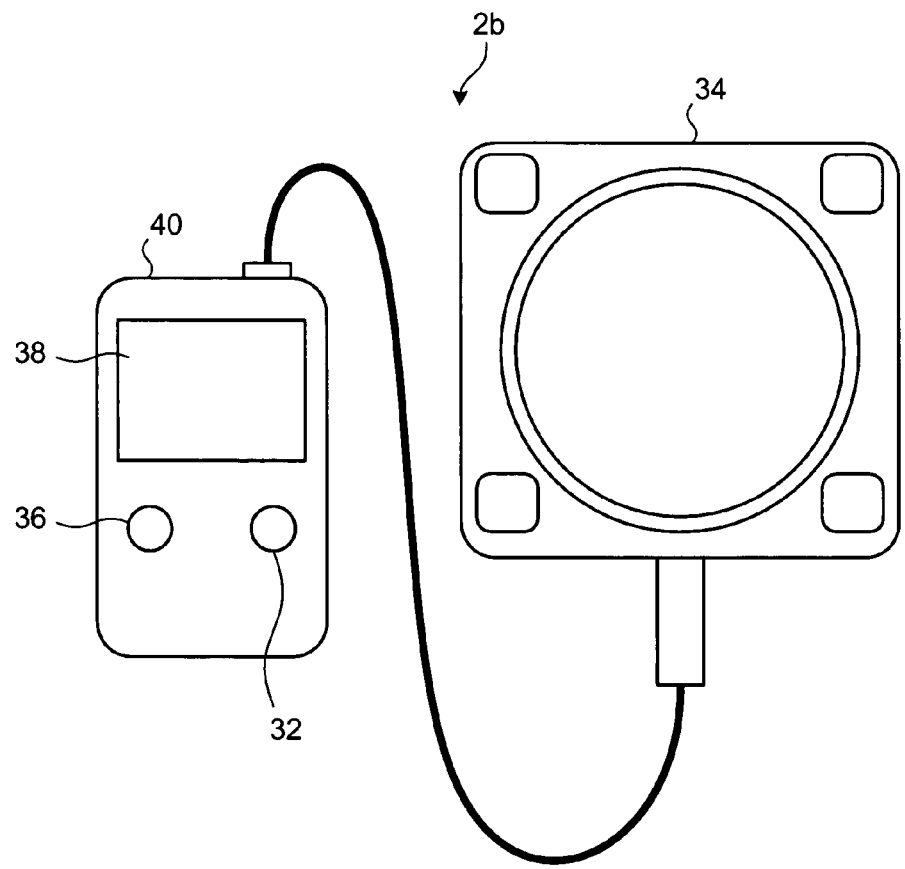
FIG. 11 is a configuration view showing one example of an external configuration of the receiving main body unit shown in FIG. 1.

The receiving main body unit 2b according to the second embodiment is connected with the power supplying coil 34 and is configured by a receiving housing 40 having the power switch 32, the input switch 36, and the display device 38 on the surface, and other components on the inside, as shown in the external configuration of FIG. 11 and the like. In this embodiment, the power supplying coil 34 is brought close to the subject 1, and the input switch 36 is pushed, thereby generating the magnetic field in the power supplying coil 34, and supplying power to the indwelling apparatus 5 to be hereinafter described that has been swallowed by the subject 1.

The external monitoring device 4 displays the body cavity image and the like imaged by the capsule endoscope 3, and the controller 51 has a configuration of a work station and the like for displaying image on the display device 52 based on the data received by the wireless device 50, as shown in FIG. 6. Specifically, the external monitoring device 4 may have a configuration of directly displaying the image by CRT display, liquid crystal display and the like, or may have a configuration of outputting the image to other medium such as a printer.

Figure 8:
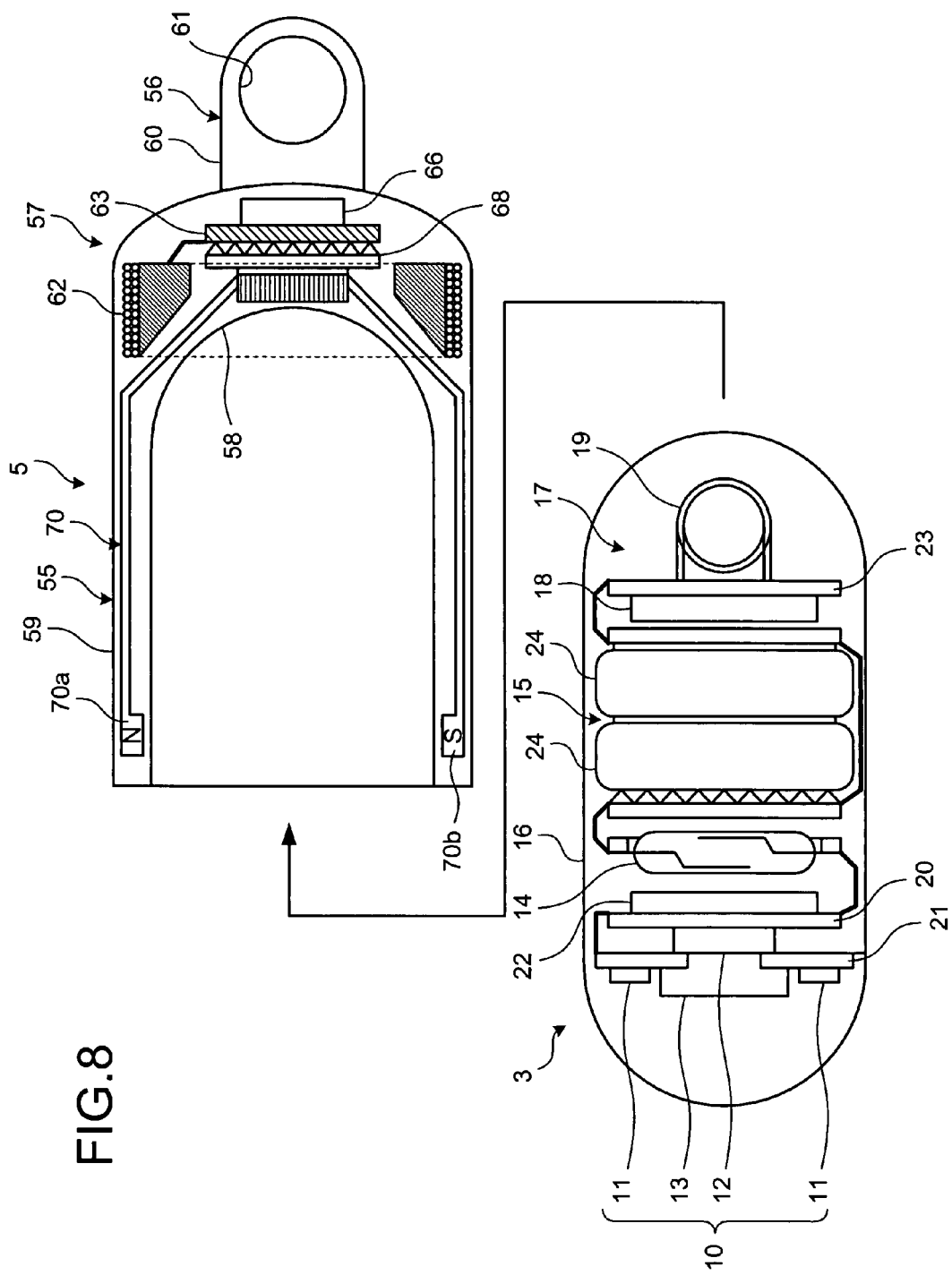
FIG. 8 is a cross sectional view showing an inner configuration of the body cavity introducing device placing system in which a capsule endoscope and an indwelling apparatus according to a second embodiment shown in FIG. 1 are separated.
Figure 9:
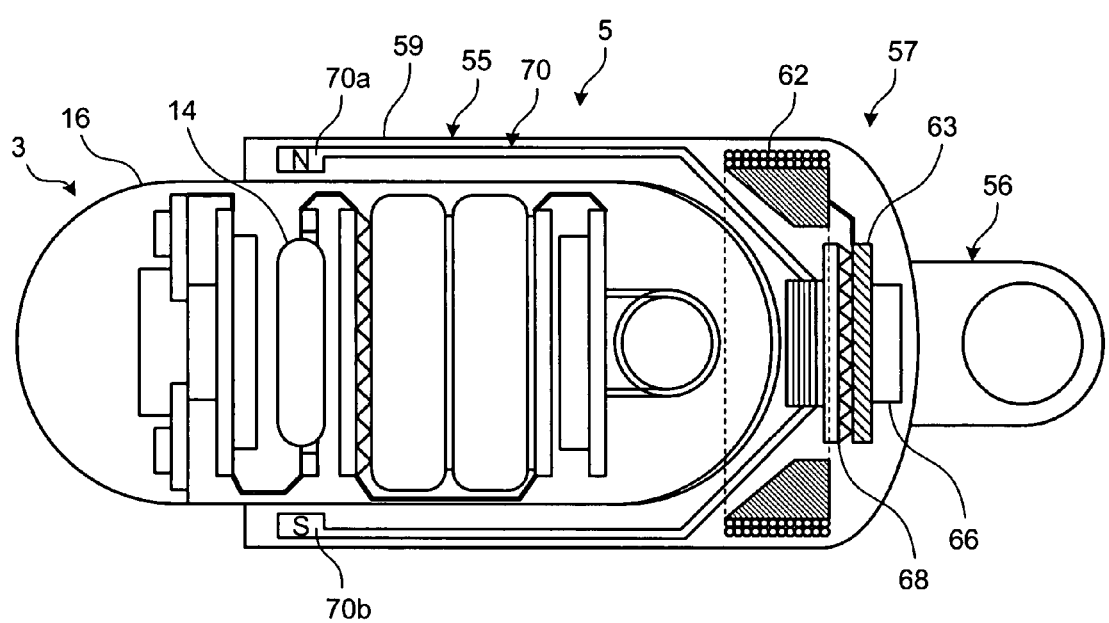
FIG. 9 is a cross sectional view showing an inner configuration of the body cavity introducing device placing system in which the capsule endoscope and the indwelling apparatus according to the second embodiment are coupled.
Figure 10:
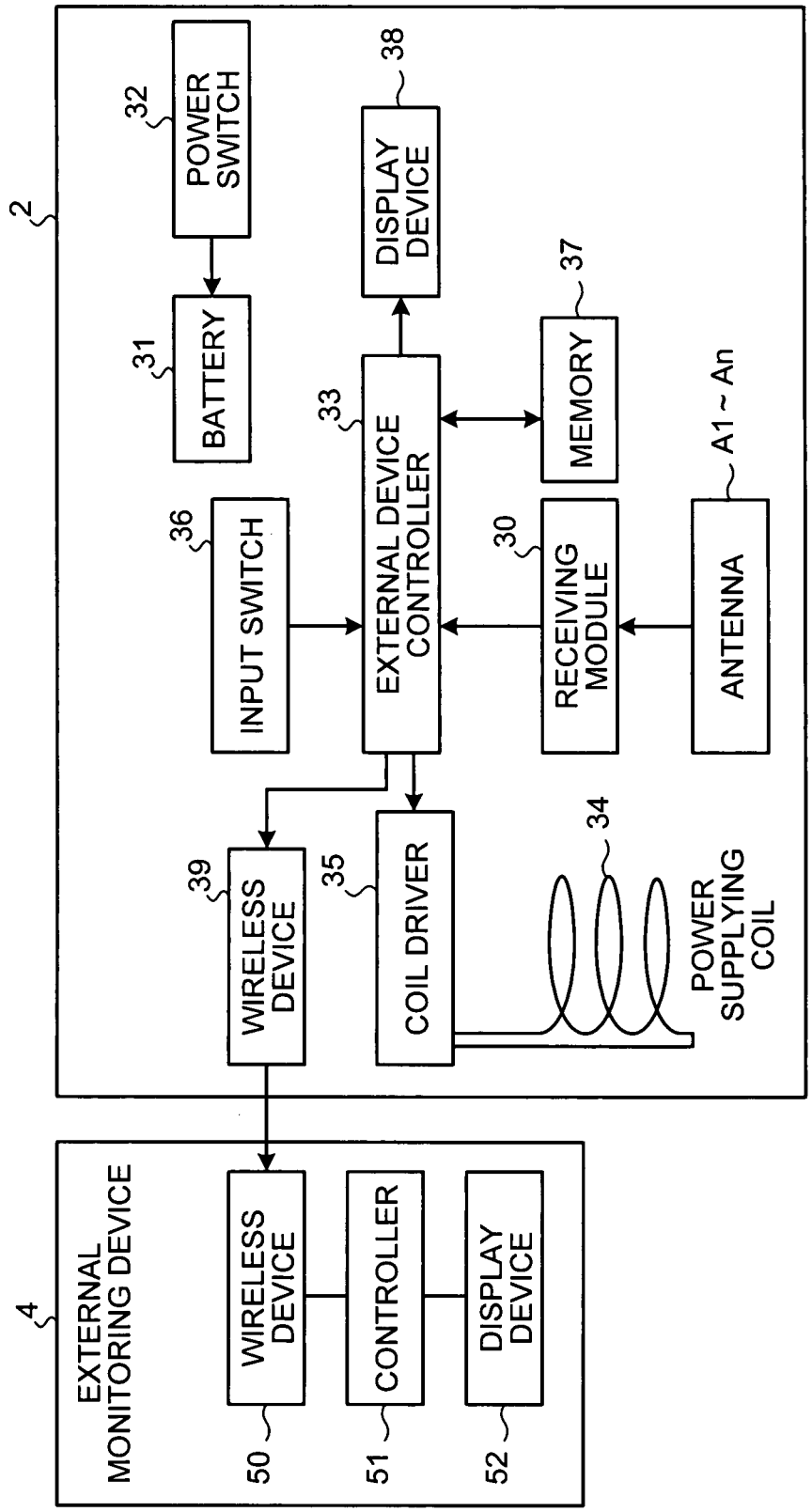
FIG. 10 is a block diagram showing an inner configuration of the receiving device and the external monitoring device according to the second embodiment.
Figure 12:
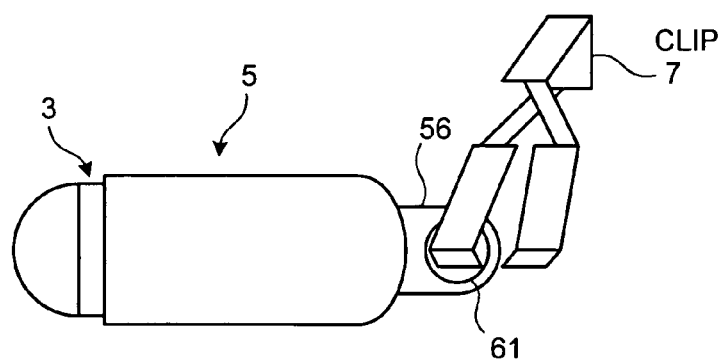
FIG. 12 is a view for explaining a case in which the capsule endoscope is placed in the body cavity.

The indwelling apparatus 5 will now be described using FIGS. 8 and 9. In the figures, the indwelling apparatus 5 includes the holding part 55 serving as a holding unit for interiorly holding the capsule endoscope 3, the binding unit 56 serving as a body cavity tissue binding unit for binding to the body cavity tissue, and the control device 57 serving as a body cavity introducing device control unit for controlling the operation of the capsule endoscope 3. The holding part 55 is made of a cylindrical tube body 59 having the bottomed bottom 58 at one end, where the inner diameter of the tube body 59 is configured to be substantially the same as the outer diameter of the core housing of the capsule endoscope 3, and the bottom 58 is configured to be substantially the same as the outer shape of the front cover housing of the capsule endoscope 3. Thus, the capsule endoscope 3 is accommodated in the tube body 59 of the holding part 55 in a holdable manner and configures the body cavity introducing device placing system with the indwelling apparatus 5, as shown in FIG. 12.

The binding part 56 is configured by a tongue shaped projecting member 60 projecting to the outer side of the bottom 58 of the holding part 55, and a circular hole 61 passing from the front to the back is formed in the projecting member 60. A clip 7 is passed through the hole 61 of the binding part 56 and clipped to the tissue of the body cavity to allow the capsule endoscope 3 to be placed in the body cavity over a long period of time.

The control device 57 includes a power supply board 63 configuring a power receiving coil 62, a rectifier 64, and a power supply device 65; and a control board 66 arranged on the power supply board 63 and configuring a reset circuit 71 and a controller 67, all of which configure the first interface (power receiving unit) for receiving power supply from the outside. The control device 57 includes a driver board 68 arranged below the power supply board 63 and configuring an electromagnetic driver 69 and a magnetic body 70, both of which configure the second interface (electromagnet).

The power receiving coil 62, arranged at the peripheral edge of the bottom 58 of the holding part 55, receives the power supplied from the power supplying coil 34 exterior to the subject 1. The magnetic body 70 is configured into a two leg shape with magnetic body ends 70a, 70b, and is formed so that both ends 70a, 70b are arranged at the same position in the reed switch 14 when the capsule endoscope 3 is held in the indwelling apparatus 5. Around the magnetic body 70A is wound a coil (not shown), and the magnetic body 70 is magnetized by flowing current to the coil from the electromagnetic driver 69, and, for example, the magnetic pole N is generated at end 70a and the magnetic pole S is generated at end 70b, thereby functioning as an electromagnet. When the magnetic body 70 functions as the electromagnet, the magnetic circuit is formed by way of the electrodes of the reed switch 14'. When the magnetic circuit is formed, the reed switch 14 is magnetized, and the contacting points contact so as to be turned ON, similar to the first embodiment.

Figure 13:
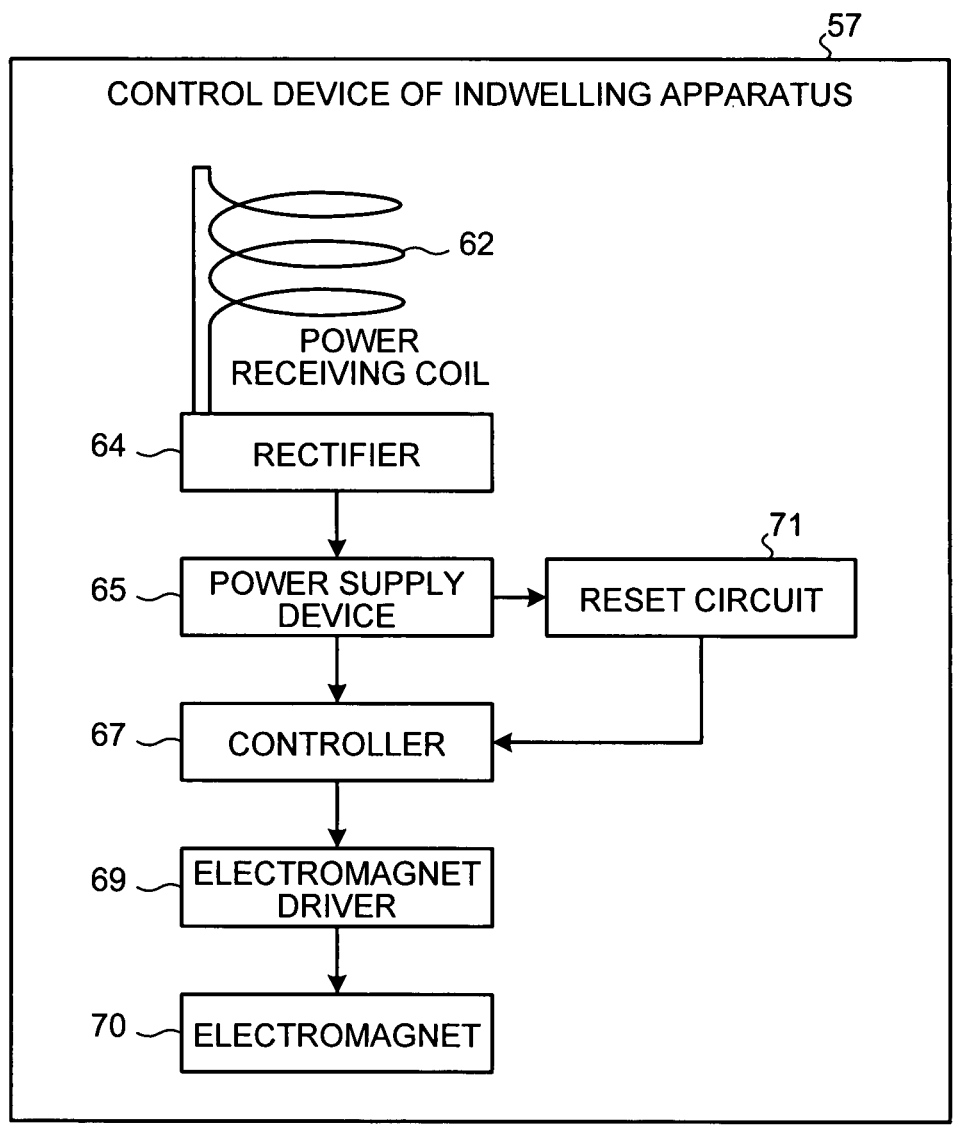
FIG. 13 is a block diagram showing a circuit configuration of the control device of the indwelling apparatus shown in FIG. 8.

The inner configuration of the control device 57 of the indwelling apparatus 5 will now be described using FIG. 13. In FIG. 13, induced electromotive force is generated when alternating power supply is made from the power supplying coil 34 of the external receiving device 2 and the current is flowed to the power receiving coil 62 in the control device 57. The current is rectified in the rectifier 64, so that a stable power is obtained from the power supply device 65. The controller 67 operation controls the electromagnet driver 69 after the system reset is performed by the reset circuit 71 and drives the magnetic body 70 (hereinafter referred to as "electromagnet 70").

Therefore, when the power supplying coil 34 of the receiving device 2 is brought close to the subject 1 as necessary and the input device 36 is pushed with the body cavity introducing device placing system placed in the body cavity of the subject 1, the power is supplied to the indwelling apparatus 5 via the power receiving coil 62 and the electromagnet 70 is drive controlled by the controller 67. The magnetic circuit is formed with the reed switch 14 by the drive control of the electromagnet 70 thereby generating the magnetic field, and thus the contacting points of the reed switch 14 contact and the power supply unit 15 supplies power to each section of the capsule endoscope 3. As a result of such power supply, the image sensor 10 of the capsule endoscope 3 operates to image the inside of the body cavity, and the image of the inside of the body cavity imaged by the image sensor 10 is transmitted to the external receiving device 2 from the wireless unit 17 and displayed on the display device 38, thereby allowing the doctors and the like to check the presence of bleeding etc.

After the observation is finished, the power supplying coil 34 is moved away from the subject 1 to stop the power supply to the indwelling apparatus 5 from the outside, and the electromagnet 70 is drive stop controlled, whereby the contacting points of the reed switch separate and turned OFF, the power supply to the capsule endoscope 3 is stopped, and the operation of the image sensor 10 and the wireless unit 17 are stop controlled.

Therefore, in the second embodiment, the external power supply from the power supplying coil of the receiving device is received at the power receiving coil to supply power to the indwelling apparatus of the body cavity introducing device placing system placed in the body cavity of the subject, thereby driving the electromagnet of the indwelling apparatus to control the reed switch of the capsule endoscope to the ON state, and operating the image sensor and the wireless unit to perform the imaging of the inside of the body cavity and the transmission of the imaged image, whereby doctors are able to observe the inside of the body cavity by moving the power supplying coil of the receiving device close to the subject and operating the capsule endoscope when observation etc. are necessary, and moving the power supplying coil away from the subject to terminate the external power supply when observation is not necessary, and thus the battery drain of the capsule endoscope is reduced. Thus, the photographing time interval is extended, and reduction of unnecessary image data and long time drive of the capsule endoscope are achieved in the present embodiment.

In The second embodiment, the operation control of the capsule endoscope is performed from the outside since the power is externally supplied to the indwelling apparatus, and thus the versatility can be enhanced. Furthermore, the operation of the capsule endoscope adapted to the purpose of placement is realized with the control from the indwelling apparatus since the capsule endoscope is operated as necessary in the embodiment.

Third Embodiment

Figure 14:
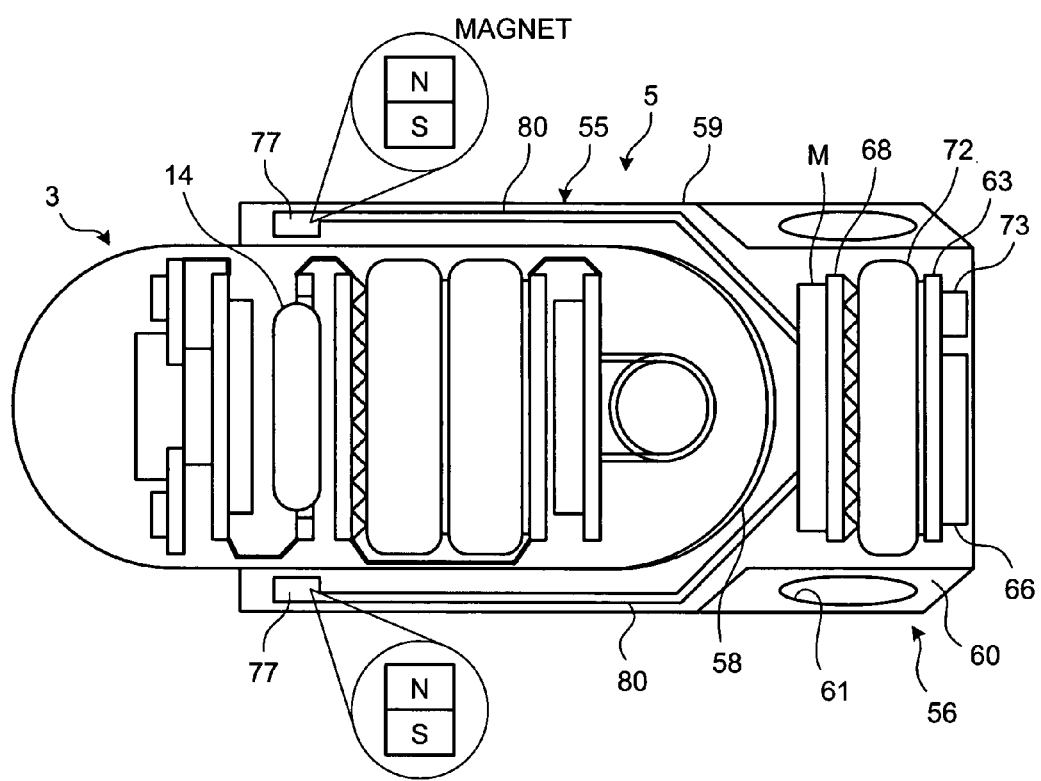
FIG. 14 is a cross sectional view showing an inner configuration of the body cavity introducing device placing system in which a capsule endoscope and an indwelling apparatus according to a third embodiment are coupled.
Figure 15:
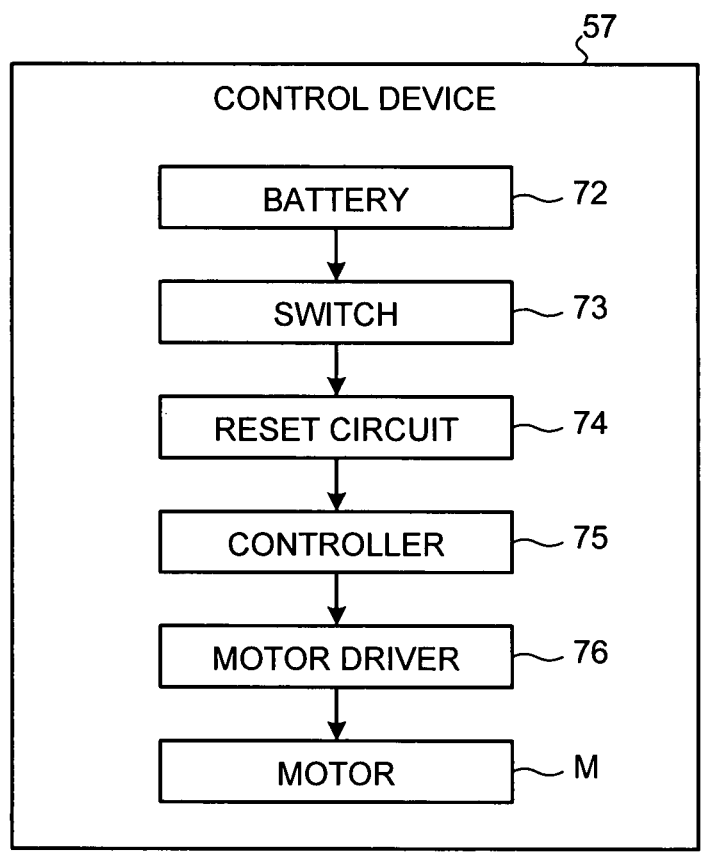
FIG. 15 is a block diagram showing a circuit configuration of the control circuit of the indwelling apparatus shown in FIG. 14.

FIG. 14 is a cross sectional view showing an inner configuration of the body cavity introducing device placing system in which the capsule endoscope and the indwelling apparatus are coupled, and FIG. 15 is a block diagram showing a circuit configuration of the control circuit of the indwelling apparatus shown in FIG. 14. In FIG. 14, the present embodiment differs from the first embodiment in that a permanent magnet 77 is used as the second interface in place of the electromagnet.

In other words, in the third embodiment, the control device 57 includes, in addition to the first interface including an optical sensor 73 serving as a light detecting unit, and a control board 66 configuring a reset circuit 74 and the controller 75, a second interface (magnetic body and movable part for moving the magnetic body) including a driver board 68 arranged below the power supply board 63 and configuring the motor driver 76, a motor M drive controlled by the motor driver 76, and a permanent magnet 77 connected to the motor M by way of a shaft 80.

The optical sensor 73 is arranged at the distal end on the bottom 58 side of the holding part 55, similar to the first embodiment, and has a function of a switch of detecting the light irradiated from the outside and allowing the power. supply from the battery 72. The shaft 80 is configured into a two leg shape, and the permanent magnet 77 of N pole and S pole is arranged at the respective distal end. The shaft 80 is formed so that the permanent magnets 77 on both ends are arranged at the same position in the reed switch 14 when the capsule endoscope 3 is held in the indwelling apparatus 5. The motor M rotates the permanent magnet at both ends of the shaft 80 in the circumferential direction of the capsule endoscope 3. The binding part 56 is the same as in the first embodiment, and thus the description thereof will not be repeated.

The inner configuration of the control device 57 of the indwelling apparatus 5 will now be described using FIG. 15. With reference to FIG. 15, before the capsule endoscope 3 and the indwelling apparatus 5 are swallowed by the subject 1, the control device 57 has the optical sensor (switch) 73 irradiated with light from the outside in advance so as to be activated and then swallowed by the subject 1. When power is supplied from the battery 72, the system reset is performed by the reset circuit 74, and thereafter, the controller 75 operation controls the motor driver 76 at every constant time interval to have the motor M rotate the shaft 80 in the circumferential direction of the capsule endoscope 3 thereby moving the permanent magnet 77 to the position where the reed switch 14 is turned ON. According to the movement control of the permanent magnet 77, a magnetic circuit is formed with the reed switch 14 and the magnetic field is generated, whereby the contacting points of the reed switch 14 contact and the power is supplied from the power supply unit 15 to each section of the capsule endoscope 3, similar to the first embodiment.

In The third embodiment, the indwelling apparatus 5 must be activated in advance before being swallowed since the capsule endoscope 3 cannot be operation controlled after the body cavity introducing device placing system is swallowed by the subject 1, and after being swallowed, the indwelling apparatus 5 operation controls the capsule endoscope 3 at every constant time interval to perform the imaging of the image inside the body cavity by means of the image sensor and the transmission of the image data by means of the wireless unit. In other words, in the present embodiment, a command for performing the operation control of the capsule endoscope 3 at a constant time interval is programmed in the controller 75, and a command control of repeating the above operation control at a constant time interval of once every 30 minutes or one hour etc. is performed.

Therefore, in the third embodiment, when the optical sensor having a switch function detects the light, the controller performs the drive control of the motor at every constant time interval to move the permanent magnet to the position where the reed switch of the capsule endoscope is turned ON, thereby operating the image sensor and the wireless unit to perform the imaging of the inside of the body cavity and transmission of the imaged image, and thus the inside of the body cavity is observed by moving the permanent magnet closer to the position where the reed switch is turned ON and operating the capsule endoscope when observation is necessary, and the operation control is performed to move the permanent magnet away from the reed switch when observation is not necessary, thus reducing the battery drain of the capsule endoscope. The photographing time interval is extended, and reduction of unnecessary image data and long time drive of the capsule endoscope are achieved, similar to the first embodiment.

Figure 16:
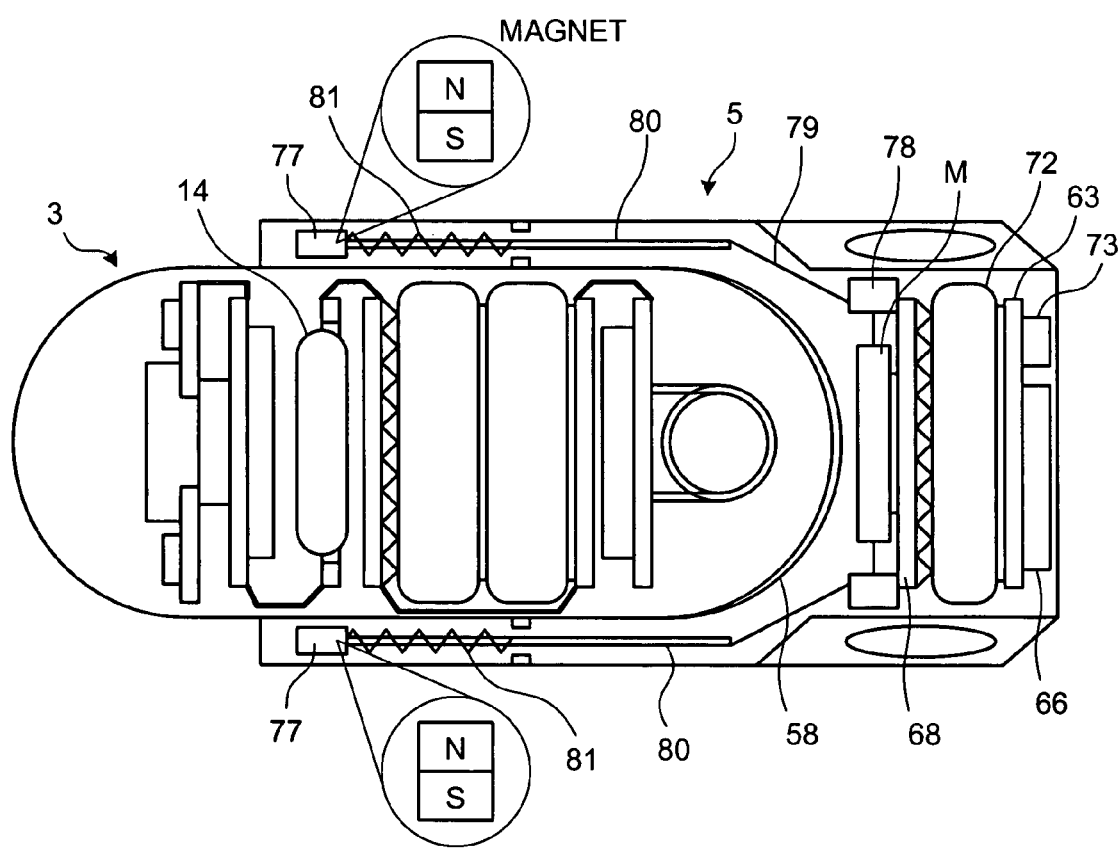
FIG. 16 is a cross sectional view showing an inner configuration of the body cavity introducing device placing system in which a capsule endoscope and an indwelling apparatus according to a modification of the third embodiment are coupled.

FIG. 16 is a cross sectional view showing an inner configuration of the body cavity introducing device placing system in which the capsule endoscope and the indwelling apparatus according to modification 1 of the third embodiment are coupled. The modification differs from The third embodiment in that the permanent magnet 77 is movement controlled in the longitudinal direction of the capsule endoscope 3 as opposed to the third embodiment in which the permanent magnet 77 is rotation controlled in the circumferential direction of the capsule endoscope 3. In order to realize the movement control, a pulley 78 with a rope 79 connected to the rotating shaft of the motor is arranged in modification 1, and the shaft 80 connected to the distal end of the rope 79 is moved in the right direction in the figure to move the permanent magnet at the distal end away from the position where the reed switch 14 is turned ON. When the motor stops, the shaft 80 is moved in the left direction in the figure by the biasing force of the spring 81, and the permanent magnet 77 at the distal end moves closer to the position where the reed switch 14 is turned ON.

Furthermore, in modification 1, when the optical sensor detects the light, the controller performs the stop control of the motor at every constant time interval to move the permanent magnet to the position where the reed switch of the capsule endoscope is turned ON, thereby operating the image sensor and the wireless unit to perform the imaging of the inside of the body cavity and the transmission of the imaged image, and thus the inside of the body cavity is observed by moving the permanent magnet closer to the position where the reed switch is turned ON and operating the capsule endoscope when observation is necessary, and the operation control is performed to move the permanent magnet away from the reed switch when observation is not necessary, thus obtaining effects similar to the third embodiment.

Similar effects are obtained with the configuration of the reed switch described in the first embodiment where the contacting points contact and the OFF state is obtained when the magnetic field is applied, and the contacting points separate and the ON state is obtained when the magnetic field is not applied, and control is performed to move the permanent magnet away from the ends of the reed switch so that the contacting points of the reed switch separate when observation is necessary, and to move the permanent magnet closer to the ends of the reed switch so that the contacting points of the reed switch contact when observation is not necessary.

Fourth Embodiment

Figure 17:
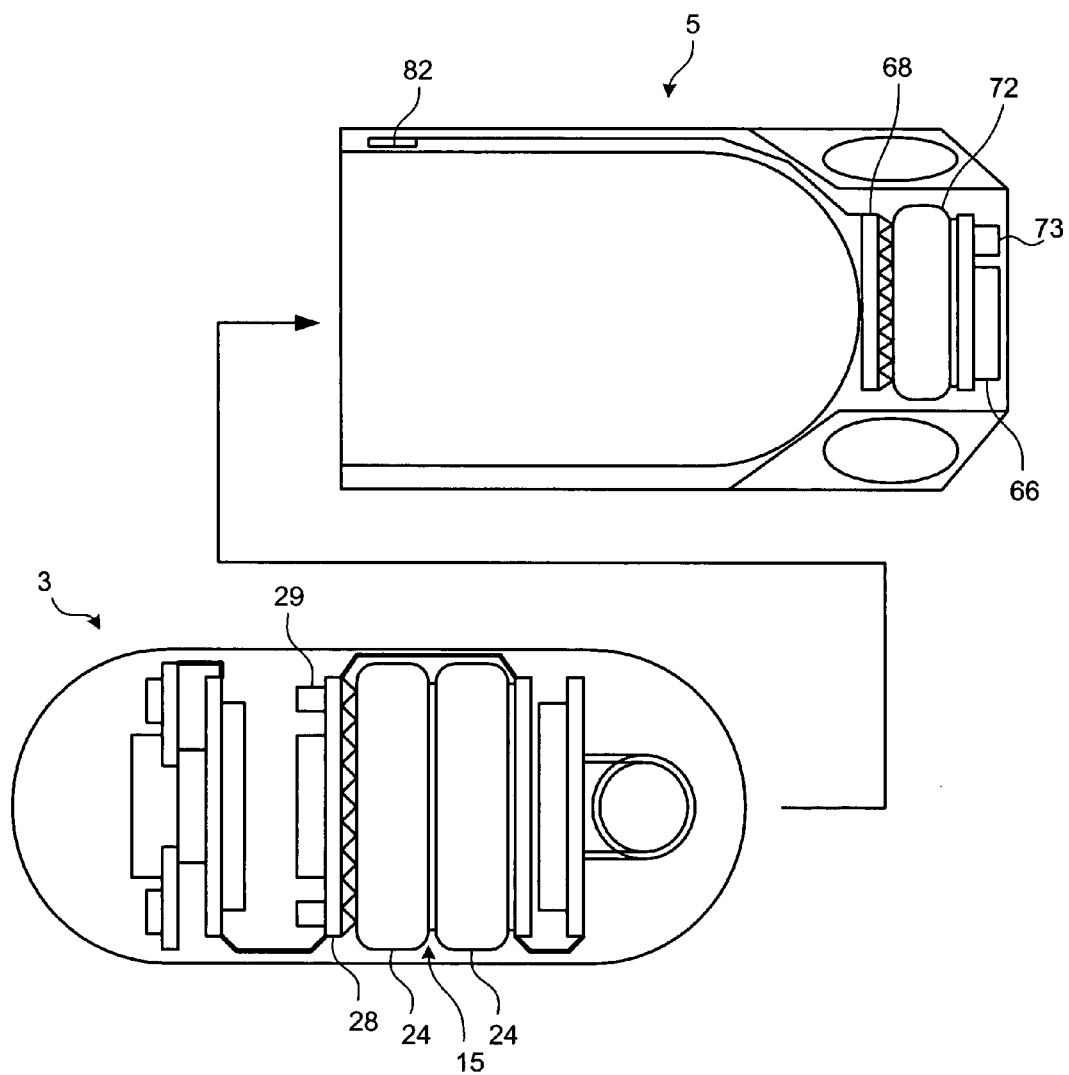
FIG. 17 is a cross sectional view showing an inner configuration of the body cavity introducing device placing system in which a capsule endoscope and an indwelling apparatus according to a fourth embodiment are separated.
Figure 18:
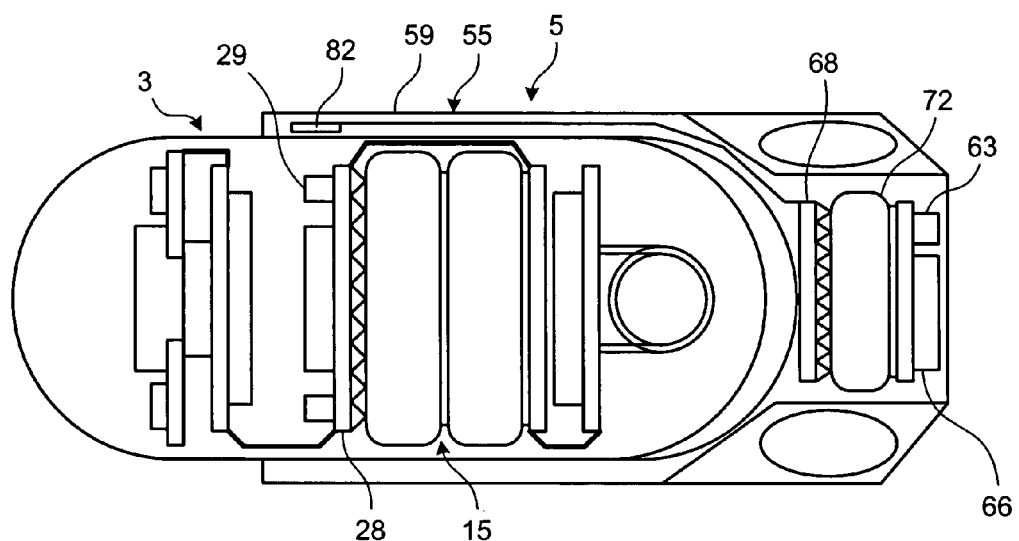
FIG. 18 is a cross sectional view showing an inner configuration of the body cavity introducing device placing system in which a capsule endoscope and an indwelling apparatus according to the fourth embodiment are coupled.

FIG. 17 is a cross sectional view showing an inner configuration of the body cavity introducing device placing system in which the capsule endoscope and the indwelling apparatus according to a fourth embodiment are separated, and FIG. 18 is a cross sectional view showing an inner configuration of the body cavity introducing device placing system in which the capsule endoscope and the indwelling apparatus according to the fourth embodiment are coupled. The fourth embodiment differs from The third embodiment in that an optical sensor 29 serving as a light detecting unit is arranged on the electrode board 28 of the battery 24 of the capsule endoscope 3 in place of the reed switch 14. The optical sensor 29 has a function of a power switch. An LED 82 and the like is arranged as a light emitting element for irradiating an infrared ray in the tubular body 59 of the holding part 55 at the same position as the optical sensor 29 when the capsule endoscope 3 is held in the indwelling apparatus 5, and the LED is operated with an LED driver 83 of the driver board 68. The LED 82 and the LED driver 83 configure the second interface, and the optical sensor 73, the reset circuit 74, and the controller 75 configure the control device 57.

Figure 19:
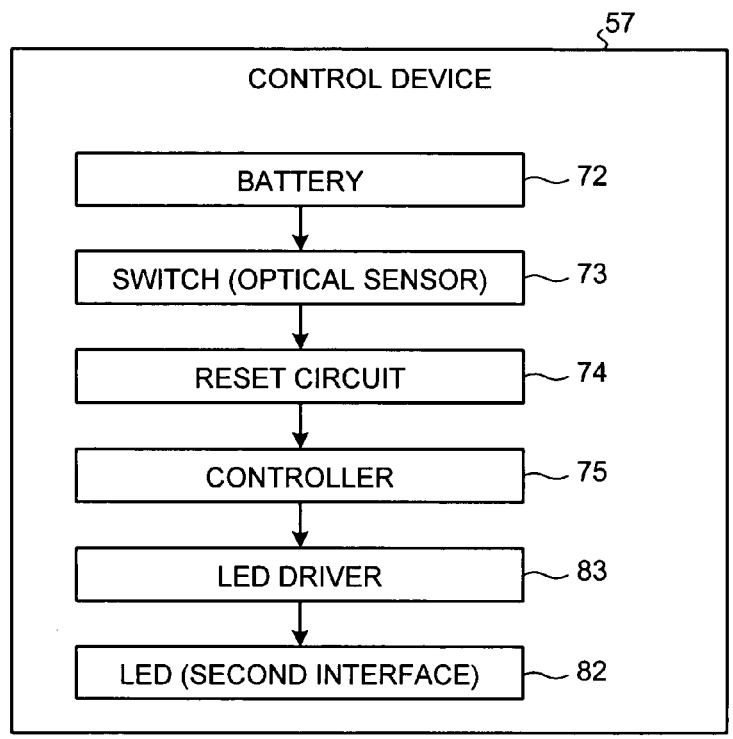
FIG. 19 is a block diagram showing a circuit configuration of a control circuit of the indwelling apparatus shown in FIG. 17.

The inner configuration of the control device 57 of the indwelling apparatus 5 will now be described using FIG. 19. With reference to FIG. 19, before the capsule endoscope 3 and the indwelling apparatus 5 are swallowed by the subject 1, the control device 57 has the optical sensor (switch) 73 irradiated with the light from the outside in advance so as to be activated and then swallowed by the subject 1. When power is supplied from the battery 72, the system reset is performed by the reset circuit 74, and thereafter, the controller 75 operation controls the LED driver 83 at every constant time interval to light the LED 82. According to the lighting control of the LED 82, the optical sensor 29 detects the light and is turned ON, whereby power is supplied from the power supply unit 15 to each section of the capsule endoscope 3.

In The fourth embodiment as well, the controller 75 performs the command control of repeating the operation control of the capsule endoscope 3 at every constant time interval to perform imaging of the image inside the body cavity by means of the image sensor and the transmission of the image data by means of the wireless unit at every constant time interval, similar to the third embodiment.

Therefore, in the fourth embodiment, when the optical sensor having the switch function of the indwelling apparatus detects light, the controller drive controls the LED at every constant time interval to light the LED, the optical sensor having the switch function of the capsule endoscope detects the light and operates the image sensor and the wireless unit to perform the imaging of the inside of the body cavity and the transmission of the imaged image, whereby the LED is lighted and the light is detected by the optical sensor to operate the capsule endoscope and allow the observation of the inside of the body cavity when observation is necessary, and the lighting of the LED is controlled and operation control is performed by way of the optical sensor when the observation is not necessary, and thus the battery drain of the capsule endoscope is reduced. Therefore, the photographing time interval is extended, and reduction of unnecessary image data and long time drive of the capsule endoscope are achieved in the fourth embodiment, similar to the first embodiment.

Figure 20:
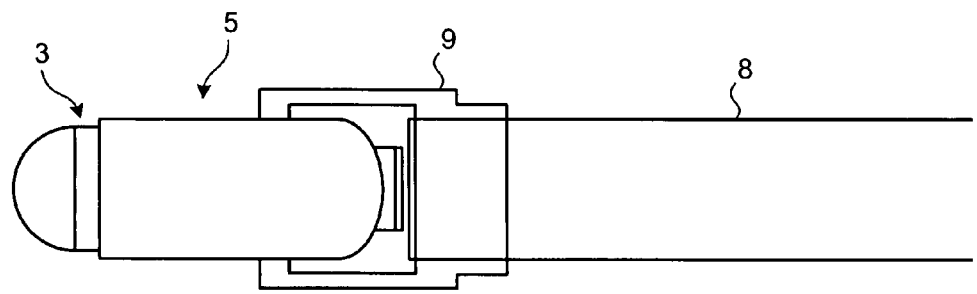
FIG. 20 is a view showing a case in which the capsule endoscope is held by the endoscope, explaining a modification of the fourth embodiment.

FIG. 20 is a view showing a case in which the capsule endoscope 3 is held by the endoscope 8, explaining modification 1 of the fourth embodiment. In the modification, an inner configuration of the capsule endoscope 3 and the indwelling apparatus 5 is the same as The fourth embodiment, but the optical sensor 73 is used as an illumination intensity sensor for detecting the illumination intensity of the light, after operating the optical sensor 73 as the switch and turning ON the power of the control device 57. If the illumination intensity detected by the optical sensor 73 is higher than a certain level, the rate of imaging of the body cavity image by means of the image sensor and transmission of the image data by means of the wireless unit of the capsule endoscope 3 is set fast, whereas when the illumination intensity detected at the optical sensor 73 is lower than the certain level, the rate is set slow.

In other words, when the body cavity introducing device placing system is introduced into the subject 1 while being held at the hood 9 arranged at the distal end of the endoscope 8, as shown in FIG. 20, the light irradiated from the endoscope 8 is detected by the optical sensor 73 of the indwelling apparatus 5, and thus the detected illumination increases, and the illumination of the light detected by the light sensor 73 decreases after the endoscope 8 placed in the body cavity is taken out from the body cavity. Therefore, in this modification, a program for performing imaging and transmission of the image at a fast rate when the illumination intensity is high for example, imaging is performed once every 0.5 seconds with the capsule endoscope constantly turned ON, is programmed in the controller 75, and a command for performing imaging and transmission of the image at slow rate when the illumination intensity is low is programmed, and a command control of repeating the above operation control at the time interval of once every 30 minutes or once an hour etc. is performed.

The optical sensor 29 is configured so as to detect the illumination intensity and a function of changing the illumination intensity is provided to the LED 82, so that the illumination intensity detection of the LED 82 at the optical sensor 29 becomes possible by changing the illumination intensity in time of operation controlling the LED 82. In the system control circuit 27 of the capsule endoscope 3, a control of changing the rate according to the difference in the illumination intensity information detected by the optical sensor 29 is incorporated, whereby imaging and transmission of the image are performed with the rate changed.

In modification 1, the control state (rate) of the capsule endoscope can be changed with the input to the optical sensor, and thus effects similar to the fourth embodiment are obtained, and further, the versatility of the system is enhanced.

The timing of acquiring the information of the inside of the body cavity is controlled by changing the rate of imaging and transmission of the image in the fourth embodiment, but the interval of imaging and transmission of the image can be changed to control the timing of acquiring the information of the inside of the body cavity even by changing the time interval of ON and OFF of the optical sensor having the function of the power switch without changing the rate.

As another modification 2 of the fourth embodiment, a magnetic sensor serving as a magnetic detecting unit may be arranged in place of the optical sensor 73 of the indwelling apparatus 5. In this case, the image sensor and the wireless unit of the capsule endoscope are operated to perform the imaging of the inside of the body cavity and the transmission of the imaged image, similar to the fourth embodiment, by moving the permanent magnet closer to the indwelling apparatus 5 swallowed from the outside of the subject 1, and detecting the magnetism of the permanent magnet with the magnetic sensor having the switch function, thereby obtaining the effects similar to the fourth embodiment.

As another modification 3 of the fourth embodiment, a wireless device serving as a wireless receiving unit may be arranged in place of the optical sensor 73 of the indwelling apparatus 5. In this case, the image sensor and the wireless unit of the capsule endoscope are operated to perform the imaging of the inside of the body cavity and the transmission of the imaged image, similar to the fourth embodiment, by transmitting a control command signal to the indwelling apparatus 5 from the external wireless device and having the controller 75 perform the control based on the command signal upon receiving the command signal at the wireless device of the indwelling apparatus 5, thereby obtaining effects similar to the fourth embodiment.

In modification 3, the operation control of the capsule endoscope is performed without malfunctioning by setting the magnetic sensor (magnetic switch) of the indwelling apparatus 5 lower with respect to the setting of the strength of the magnetic field that reacts even when the power switch of the capsule-endoscope 3 is, for example, the reed switch shown in the first embodiment.

In The fourth embodiment, the function of turning ON the power of the indwelling apparatus and the function of controlling the subsequent operation are performed in a single first interface, but the present invention is not limited thereto, and a switch for turning ON the power supply and a sensor for controlling the subsequent operation may be separately configured.

Fifth Embodiment

Figure 21:
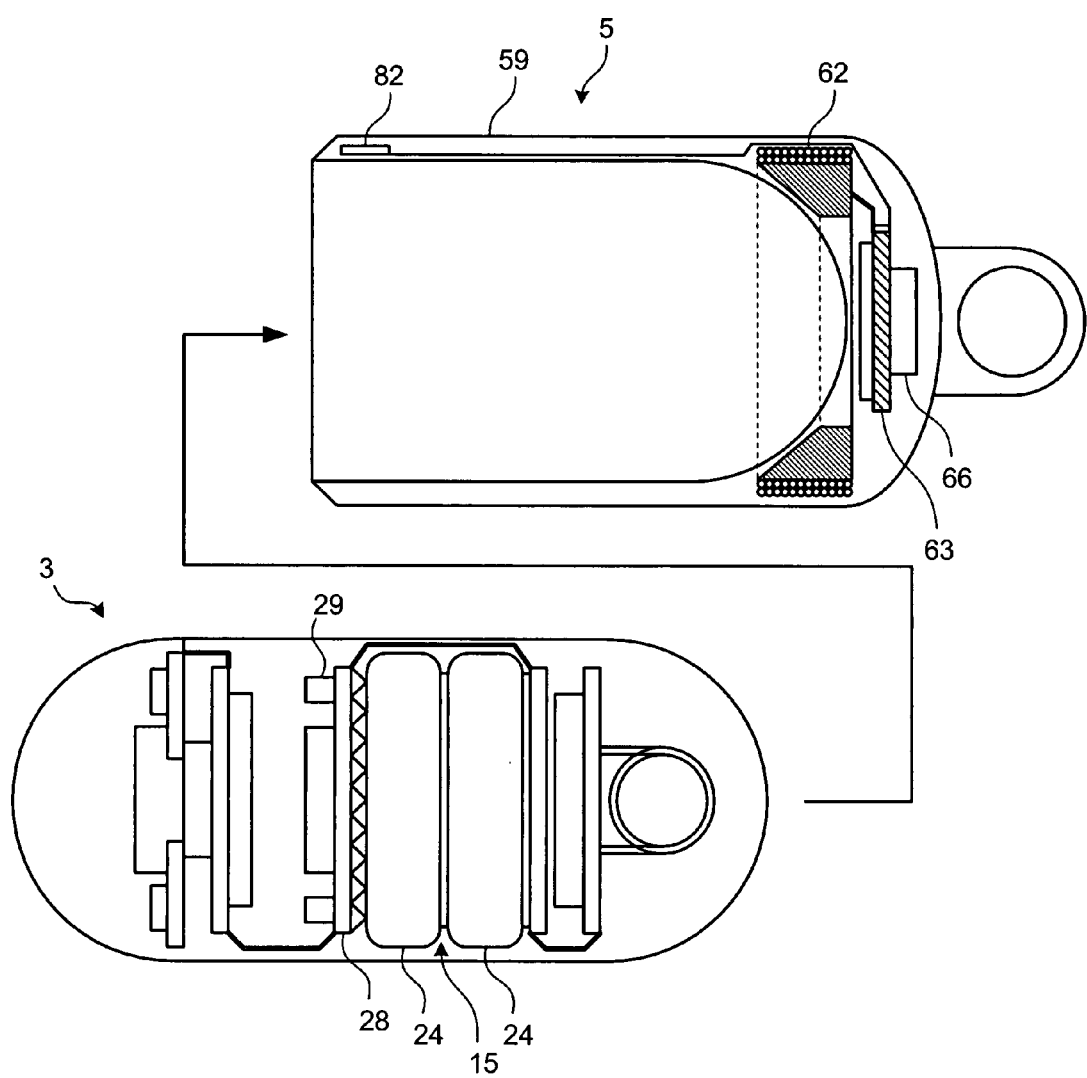
FIG. 21 is a cross sectional view showing an inner configuration of the body cavity introducing device placing system in which a capsule endoscope and an indwelling apparatus according to a fifth embodiment are separated.
Figure 22:
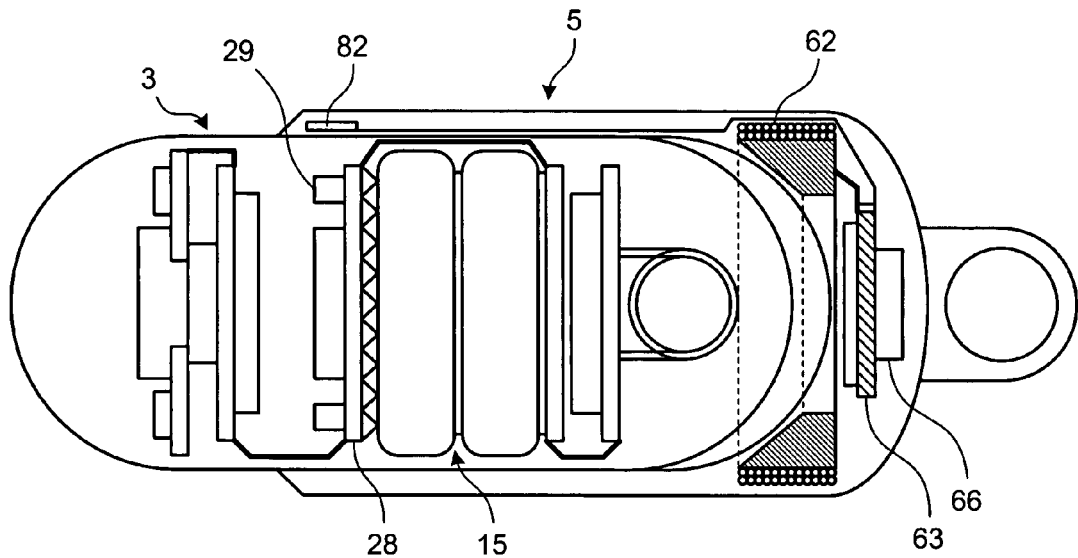
FIG. 22 is a cross sectional view showing an inner configuration of the body cavity introducing device placing system in which a capsule endoscope and an indwelling apparatus according to the fifth embodiment are coupled.

FIG. 21 is a cross sectional view showing an inner configuration of the body cavity introducing device placing system in which the capsule endoscope and the indwelling apparatus according to a fifth embodiment are separated, and FIG. 22 is a cross sectional view showing the inner configuration of the body cavity introducing device placing system in which the capsule endoscope and the indwelling apparatus according to the fifth embodiment are coupled. This embodiment has a combined configuration of the second embodiment (see FIGS. 8 and 9), and The fourth embodiment (see FIG. 18). In other words, in the fifth embodiment, the power receiving coil 62 for receiving power supplied from the power supplying coil 34 exterior to the subject 1 is arranged at the peripheral edge of the bottom 58 of the holding part 55, similar to the second embodiment. Furthermore, in the fifth embodiment, the optical sensor 29 having the function of the power switch is arranged on the electrode board 28 of the battery 24 of the capsule endoscope 3, and the LED 82 is arranged in the tubular body 59 of the holding part 55 at the same position as the optical sensor 29 when the capsule endoscope 3 is held in the indwelling apparatus 5, similar to the fourth embodiment. The power receiving coil 62 and the LED 82 are electrically connected to the power supply board 63.

Figure 23:
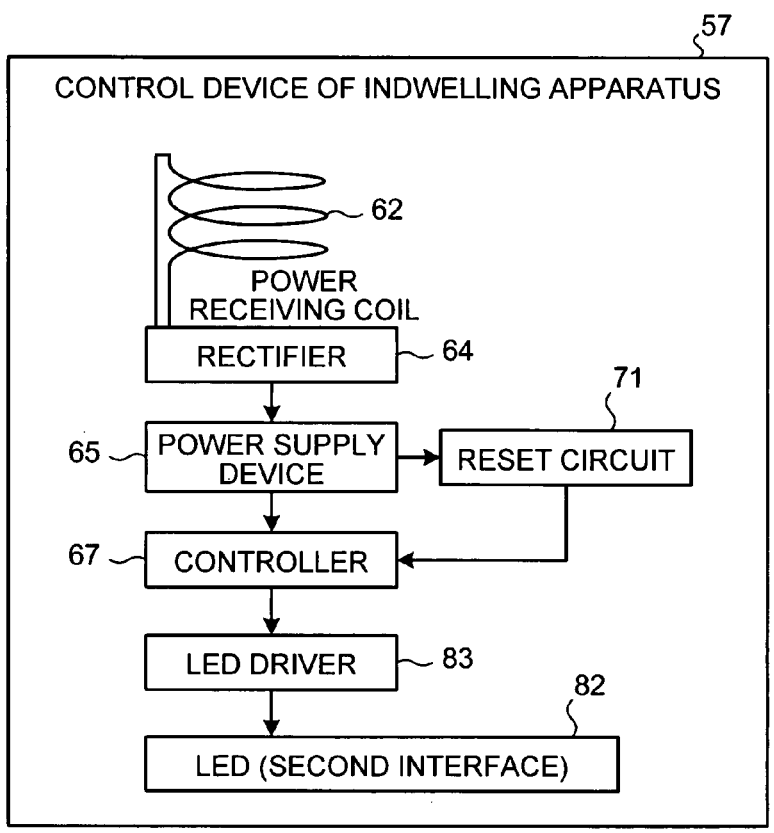
FIG. 23 is a block diagram showing a circuit configuration of a control circuit of the indwelling apparatus shown in FIG. 21.

The inner configuration of the control device 57 of the indwelling apparatus 5 will now be described using FIG. 23. In the control device 57, the inductive electromotive force is generated when the alternating power is supplied from the power supplying coil 34 of the external receiving device 2, and the current flows to the power receiving coil 62, as shown in FIG. 23. A stable power is obtained from the power supply device 65 by rectifying the current in the rectifier 64. After the system reset is performed by the reset circuit 71, the controller 67 operation controls the LED driver 83 at every constant time interval to light the LED 82. According to the lighting control of the LED 82, the optical sensor 29 detects the light and is turned ON, and the power is supplied from the power supply unit 15 to each section of the capsule endoscope 3.

In The fifth embodiment, the external power supply from the power supplying coil of the receiving device is received at the power receiving coil, the power is supplied to the indwelling apparatus placed in the body cavity of the subject, the controller drive controls the LED to light the LED, the optical sensor having the switch function of the capsule endoscope detects light, and the image sensor and the wireless unit are operated to perform imaging of the inside of the body cavity and transmission of the image, whereby doctors are able to observe the inside of the body cavity by moving the power supplying coil of the receiving device closer to the subject and operating the capsule endoscope when observation and the like is necessary, and moving the power supplying coil away from the subject and terminating the external power supply when observation is not necessary, and thus the battery drain of the capsule endoscope is reduced. Thus, in the fifth embodiment, the photographing time interval is extended, and reduction of unnecessary image data and long time drive of the capsule endoscope are achieved.

In The fifth embodiment, the operation control of the capsule endoscope is externally performed by supplying power to the indwelling apparatus from the outside, and versatility is enhanced. In this embodiment, the capsule endoscope is operated, as necessary, whereby the operation of the capsule endoscope adapted to the purpose of placement is realized with the control from the indwelling apparatus.

Sixth Embodiment

Figure 24:
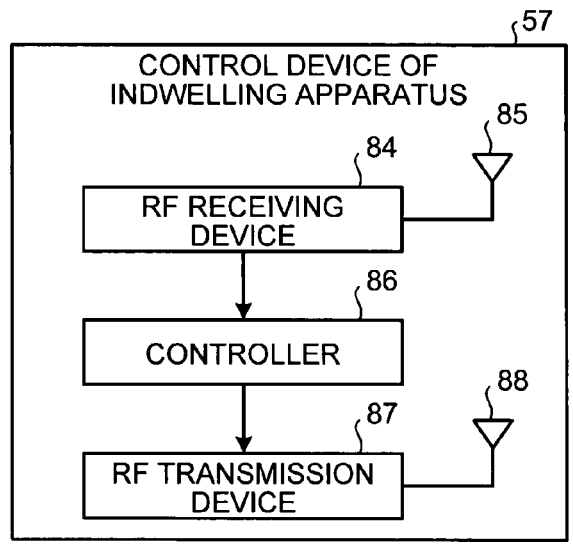
FIG. 24 is a block diagram showing a circuit configuration of a control circuit of the indwelling apparatus according to a sixth embodiment.
Figure 25:
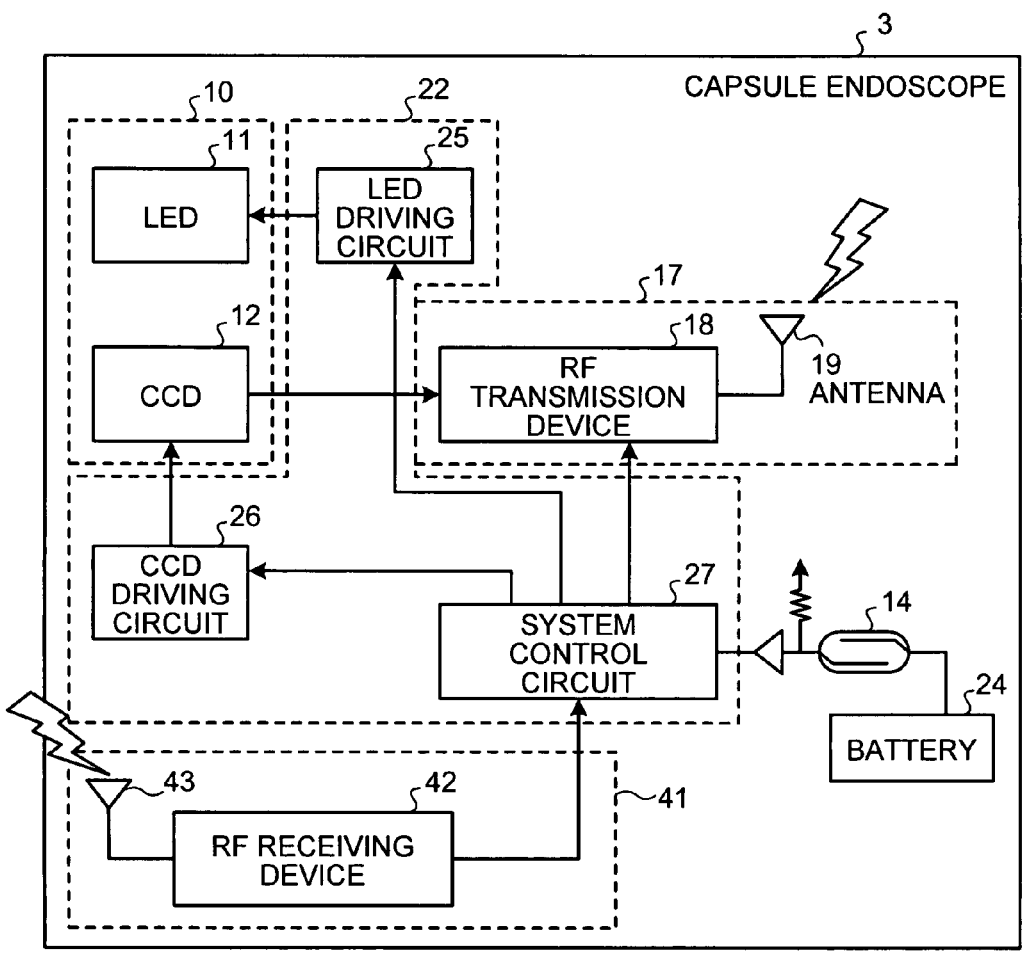
FIG. 25 is a block diagram showing a. circuit configuration of a capsule endoscope according to the sixth embodiment.

FIG. 24 is a block diagram showing a circuit configuration of a control circuit of the indwelling apparatus according to a sixth embodiment, and FIG. 25 is a block diagram showing a circuit configuration of the capsule endoscope according to the sixth embodiment. In The sixth embodiment, a command for instructing operation start or operation stop of the capsule endoscope 3 is transmitted as a wireless signal from the wireless device 39 of the receiving device 2 or the wireless device 50 of the external monitoring device 4 shown in FIG. 6 and the like, and the indwelling apparatus 5 receives the transmitted command and transmits an instruction command (operation start command and operation stop command with respect to capsule endoscope 3) corresponding to the relevant command to the capsule endoscope 3.

Specifically, the control device 57 of the indwelling apparatus 5 includes an RF receiving device 84, a controller 86 serving as a body cavity introducing device control unit, and a RF transmission device 87. The command modulated and transmitted as a wireless signal from the wireless device 39 or 50 is demodulated and received by the RF receiving device 84 via the antenna 85, and the controller 86 recognizes the command received by the RF receiving device 84 and outputs the instruction command corresponding to the command to the RF transmission device 87. The RF transmission device 87 demodulates the instruction command output from the controller 86 to a wireless signal, and transmits the same to the capsule endoscope 3 via the antenna 88.

In FIG. 25, the capsule endoscope 3 includes an RF receiving device 42 and an antenna 43 as a wireless unit 41, in addition to the configuration of FIG. 5. The instruction command transmitted from the indwelling apparatus 5 is demodulated and received by the RF receiving device 42 via the antenna 43, and the system controller circuit 27 recognizes the instruction command received by the RF receiving device 42 and controls the operation start or the operation stop, corresponding to the instruction command, of the LED driving circuit 25, the CCD driving circuit 26, and the RF transmission device 18. The wireless frequency of the wireless signal transmitted from the wireless device 39, 50 to the indwelling apparatus 5 and the wireless frequency of the wireless signal transmitted from the RF transmission device 87 of the indwelling apparatus to the capsule endoscope 3 are set to different frequency bands, where a band pass filter for the relevant frequency band is arranged on the receiving device side to allow reception of the wireless signal.

Therefore, in the sixth embodiment, a command for the operation start command and the operation stop command with respect to the capsule endoscope is transmitted from the receiving device and the external monitoring device exterior to the living body to the indwelling apparatus, and the instruction command corresponding to the command is transmitted from the indwelling apparatus to the capsule endoscope to perform operation start and operation sop on the capsule endoscope, and thus the operation of the capsule endoscope can be controlled from outside the living body, and the battery drain of the capsule endoscope is reduced. Thus, in the sixth embodiment, the image data is acquired only when observation is necessary, and reduction of unnecessary image data and long time drive of the capsule endoscope are achieved.

In the indwelling apparatus 5, the controller 86 of the control device 57 is configured so as to interiorly include a timer, where the operation start command and the operation stop command are set so as to be repeated at a predetermined time interval, for example, at a constant time interval of once every 30 minutes or once an hour by counting the timer with respect to the command reception from the receiving device or the external monitoring device. In this case, the capsule endoscope 3 is intermittently operated, image data is acquired only when observation is necessary, and reduction of unnecessary image data and long time drive of the capsule endoscope are achieved.

Similar to the first embodiment, a command for performing the operation control of the capsule endoscope 3 at a constant time interval, that is, a command for operation controlling the electromagnet driver 69 at a constant time interval is programmed in the controller 86, and a command control of repeating the above operation control at a constant time interval of once every 30 minutes or once an hour is performed with respect to the command reception of the operation start command from the receiving device or the external monitoring device to ON/OFF control the reed switch 14. Furthermore, the command control may be stopped with respect to the command reception of the operation stop command.

The sixth embodiment is not limited to the case of magnetism and even in the case of the LED 82 shown in the fourth embodiment and the like, a command for operation controlling the LED driver 83 at a constant time interval is programmed and a command control of repeating the above operation control at a constant time interval is performed with respect to the command reception of the operation start command from the receiving device or the external monitoring device to intermittently operate the capsule endoscope 3.

Seventh Embodiment

Figure 26:
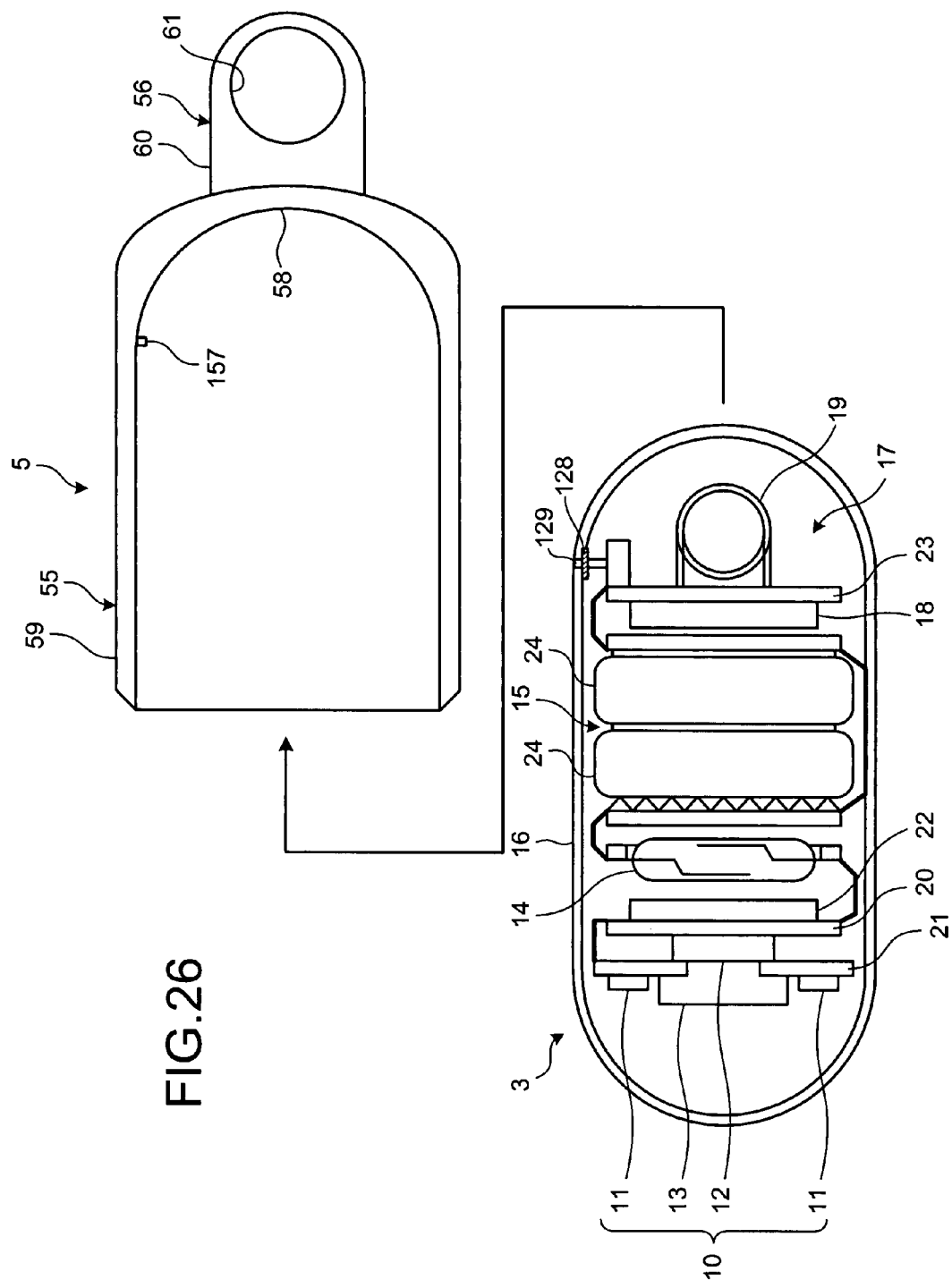
FIG. 26 is a cross sectional view showing an inner configuration of the body cavity introducing device placing system in which a capsule endoscope and an indwelling apparatus according to a seventh embodiment shown in FIG. 1 are separated.
Figure 27:
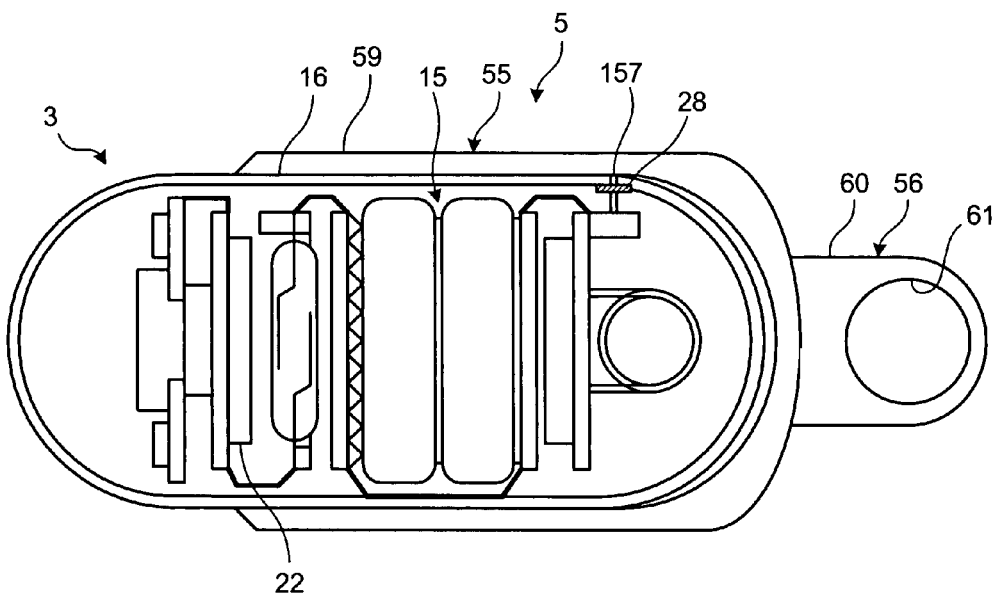
FIG. 27 is a cross sectional view showing an inner configuration of the body cavity introducing device placing system in which a capsule endoscope and an indwelling apparatus according to the seventh embodiment are coupled.
Figure 28:
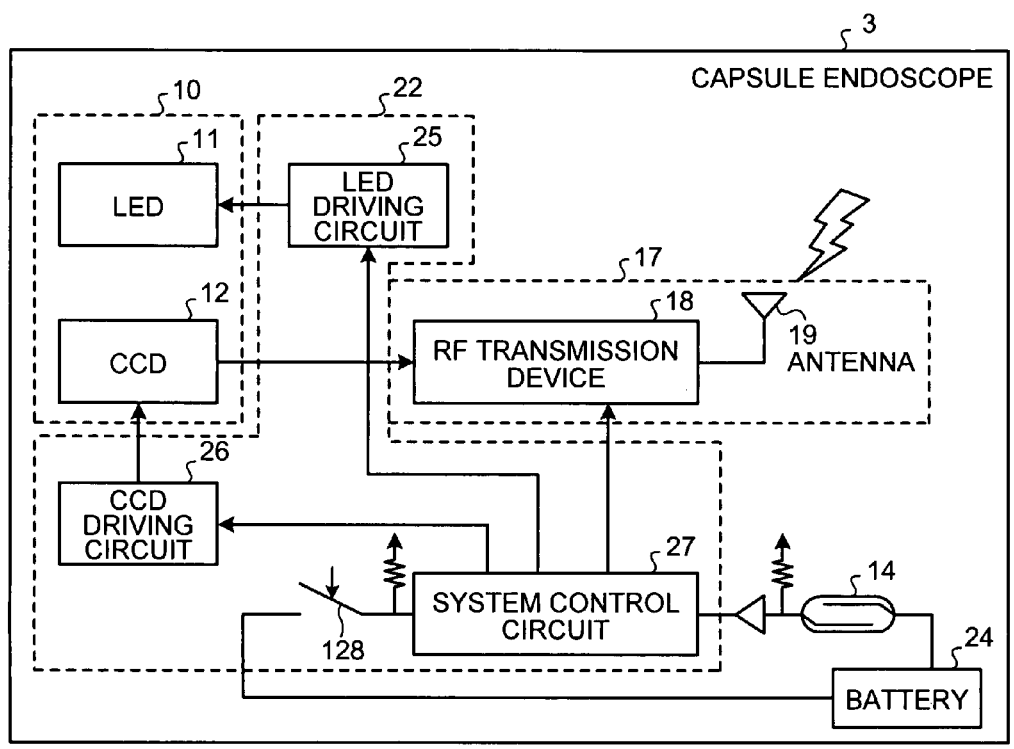
FIG. 28 is a block diagram showing a circuit configuration of a capsule endoscope shown in FIG. 26.

The body cavity introducing device placing system according to a seventh embodiment will now be described. FIG. 26 is a cross sectional view showing an inner configuration of the body cavity introducing device placing system in which the capsule endoscope and the indwelling apparatus according to the seventh embodiment shown in FIG. 1 are separated, FIG. 27 is a cross sectional view showing an inner configuration of the body cavity introducing device placing system (in vivo information acquiring device placing system) in which the capsule endoscope and the indwelling apparatus according to the seventh embodiment are coupled, and FIG. 28 is a block diagram showing a circuit configuration of the capsule endoscope shown in FIG. 26. In the subject information acquiring system, the capsule endoscope is used as one example of the subject introducing device (in vivo information acquiring device main body). In The seventh embodiment, the circuit configuration of the wireless unit 2a and the receiving main body 2b is shown as one block in FIG. 4. The circuit configuration of the receiving device 2 and the external monitoring device 4 is similar to FIG. 6, and thus the description thereof is not repeated.

The capsule endoscope 3 according to the seventh embodiment includes a mechanical button switch 128 serving as a switch unit (request input unit, operation mode switching request switch) at the vicinity of the surface of the capsule shaped housing 16, and a hole 129 formed on the surface of the capsule shaped housing 16 above the button switch 128, and a pin 157, to be hereinafter described, of the button switch 128 is pushed through the hole 129. The button switch 128 is configured so as to be turned ON when the pin 157 is pushed, and restored to the OFF state by the biasing force of the spring (not shown) and the like when the pin 157 is not pushed. Other configurations, or the image sensor 10 (LED 11, CCD 12), the optical system device 13, the reed switch 14, the power supply unit 15 (button type battery 24, 24), the capsule shaped housing 16, the wireless unit 17 (RF transmitting part 18, antenna 19), and the system control circuit 27, are similar to the first embodiment, and thus the description thereof will not be repeated.

The indwelling apparatus 5 will now be described using FIGS. 26 and 27. In the figures, the indwelling apparatus 5 includes a holding part (attachment) 55 serving as a holding unit for interiorly holding the capsule endoscope 3, a binding part 56 serving as a body cavity tissue binding unit for binding to the body cavity tissue, and a pin 157 serving as a pushing unit (request output unit, operation mode switching request unit) for pushing the button switch 128 when the capsule endoscope 3 is held by the holding part 55. The holding part 55 is made of a cylindrical tube body 59 having a bottomed bottom 58 at one end, where the inner diameter of the tube body 59 is configured to be substantially the same as the outer diameter of the core housing of the capsule endoscope 3, and the bottom 58 is configured to be substantially the same as the outer shape of the front cover housing of the capsule endoscope 3. Thus, the capsule endoscope 3 is accommodated in the tube body 59 of the holding part 55 in a holdable manner and configures the body cavity introducing device placing system with the indwelling apparatus 5, as shown in FIG. 27.

The binding part 56 is configured by a tongue shaped projecting member 60 projecting to the outer side of the bottom 58 of the holding part 55, and a circular hole 61 passing from the front to the back is formed in the projecting member (hook part) 60. Therefore, similar to FIG. 12, a clip 7 is passed through the hole 61 of the binding part 56 and clipped to the tissue of the body cavity to allow the capsule endoscope 3 to be placed in the body cavity over a long period of time.

The pin 157 is arranged projecting vertically from the inner peripheral surface of tube body 59, and engages the hole 129 of the capsule endoscope 3 when the capsule endoscope 3 is accommodated in the tube body 59 of the holding part 55 in a holdable manner to push the button switch 128 down in FIG. 27 and to turn ON the button switch 28.

The circuit configuration of the capsule endoscope 3 will now be described using FIG. 28. The seventh embodiment differs from The first embodiment in that the button switch 128 is connected to the battery 24 and the system control circuit 27, where the system control circuit 27 recognizes the operation mode of the capsule endoscope 3 by referencing the ON/OFF state of the button switch 128, for example, with the change in input voltage. In other words, when recognizing that the button switch 128 is in the OFF state, the system control circuit 27 determines that the capsule endoscope 3 is in the normal mode (first operation mode), and operation controls the image sensor 10 and the RF transmission device 18 so as to perform imaging of the inside of the body cavity with the image sensor 10 at every 0.5 seconds and transmit all image data from the RF transmission device 18. When recognizing that the button switch 128 is in the OFF state, the system control circuit 27 determines that the capsule endoscope 3 is in the placement mode (second operation mode), and operation controls the image sensor 10 and the RF transmission device 18 so as to perform imaging of the inside of the body cavity with the image sensor 10 once every five minutes and transmit all image data from the RF transmission device 18.

In The seventh embodiment, when the capsule endoscope is held in the indwelling apparatus, the pin pushes the button switch, the system control circuit recognizes the ON state of the button switch, and changes the frame rate of imaging and transmission from the normal mode of every 0.5 seconds to the placement mode of once every five minutes, whereby power consumption in the capsule endoscope is reduced, and the battery drain of the capsule endoscope is reduced. Therefore, in the seventh embodiment, the photographing time interval is extended, and reduction of unnecessary image data and long time drive of the capsule endoscope are achieved.

In The seventh embodiment, the versatility of the system is enhanced since the control state (rate) of the capsule endoscope can be changed by pushing the button switch.

Figure 29:
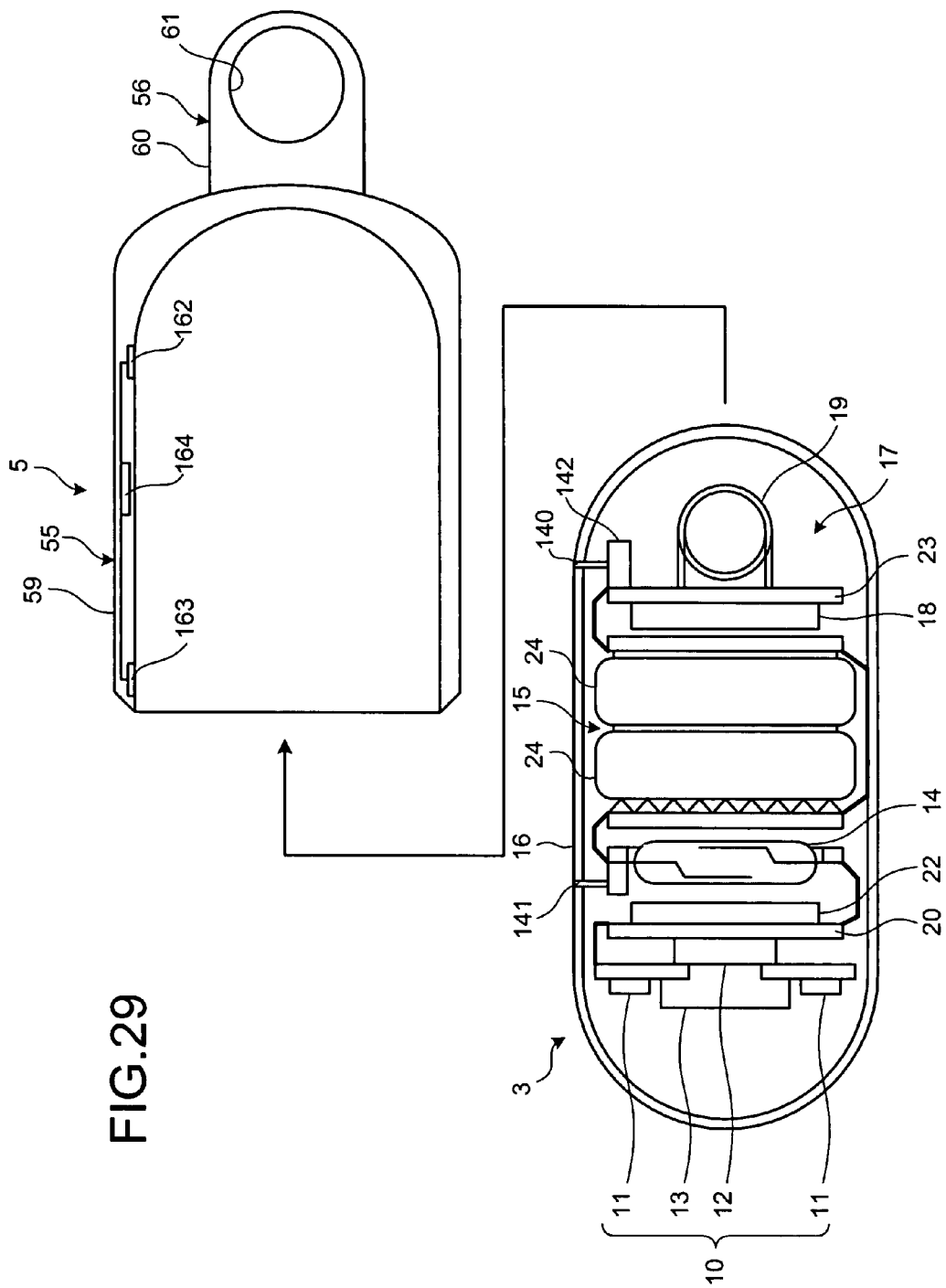
FIG. 29 is a cross sectional view showing an inner configuration of the body cavity introducing device placing system in which a capsule endoscope and an indwelling apparatus according to modification 1 of the seventh embodiment are separated.
Figure 30:
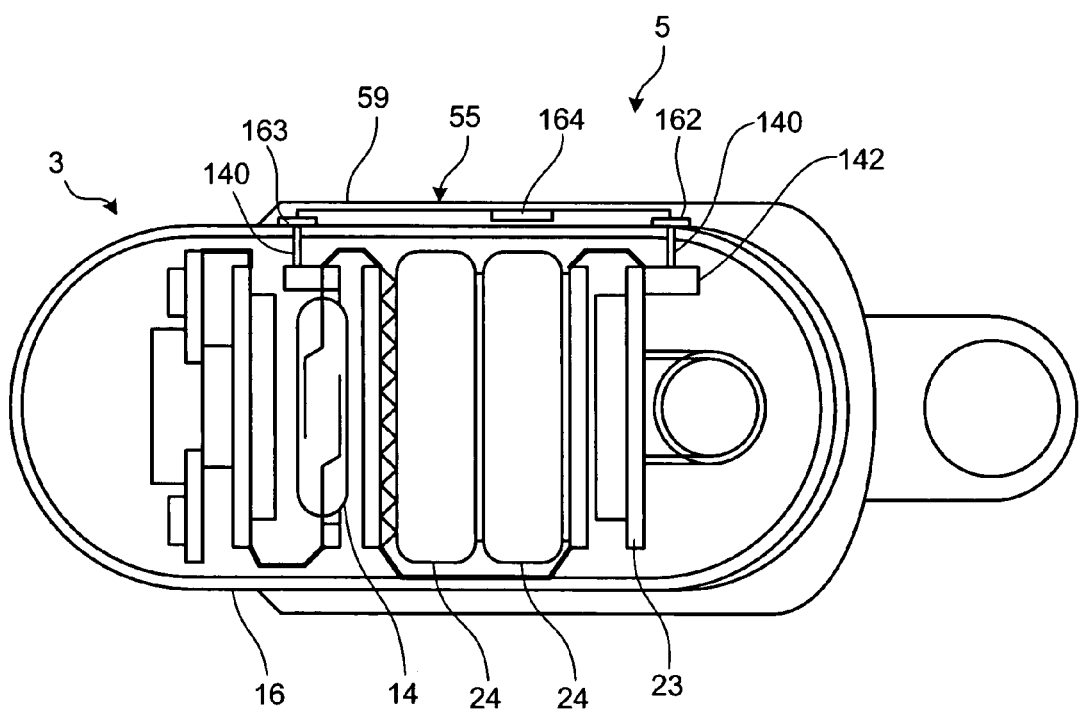
FIG. 30 is a cross sectional view showing an inner configuration of the body cavity introducing device placing system in which a capsule endoscope and an indwelling apparatus according to modification 1 are coupled.

FIG. 29 is a cross sectional view showing an inner configuration of the body cavity introducing device placing system in which the capsule endoscope and the indwelling apparatus according to modification 1 of the seventh embodiment are separated, and FIG. 30 is a cross sectional view showing an inner configuration of the body cavity introducing device placing system in which the capsule endoscope and the indwelling apparatus according to modification are coupled. In such modification, switch is performed between the normal mode and the placement mode by measuring the change in potential-.between the electrodes. In other words, in modification 1, the electrodes 140, 141 connected to the anode and the cathode of the battery 24 of the capsule endoscope 3 are arranged at predetermined positions on the surface of the capsule shaped housing 16. An electrometer 142 serving as a potential detecting unit for measuring the potential between the electrodes 140, 141 is arranged on the wireless board 23. The potential measured by the electrometer 142 is recognized by the system control circuit 27.

On the indwelling apparatus 5 side, two electrodes 162, 163 are arranged on the inner peripheral surface of the tube body 59 of the holding part 55, and the electrodes 162, 163 are connected by way of a resistor 164 serving as a potential unit having a predetermined resistance value. When the capsule endoscope 3 is accommodated in the tube body 59 of the holding part 55 in a holdable manner, the electrodes 140, 141 of the capsule endoscope 3 respectively connect to the electrodes 162, 163 of the indwelling apparatus 5, and the potential measured at the electrometer 142 changes. The system control circuit 27 recognizes the change in the potential, and switches the frame rate of imaging and transmission from the normal mode of every 0.5 seconds to the placement mode of once every five minutes.

In modification 1, when the capsule endoscope is held in the indwelling apparatus, the potential measured by the electrometer changes, which change is recognized by the system control circuit and the frame rate of imaging and transmission is changed from the normal mode of every 0.5 seconds to the placement mode once every five minutes, whereby power consumption in the capsule endoscope is reduced, and the battery drain of the capsule endoscope is reduced, similar to the first embodiment.

Figure 31:
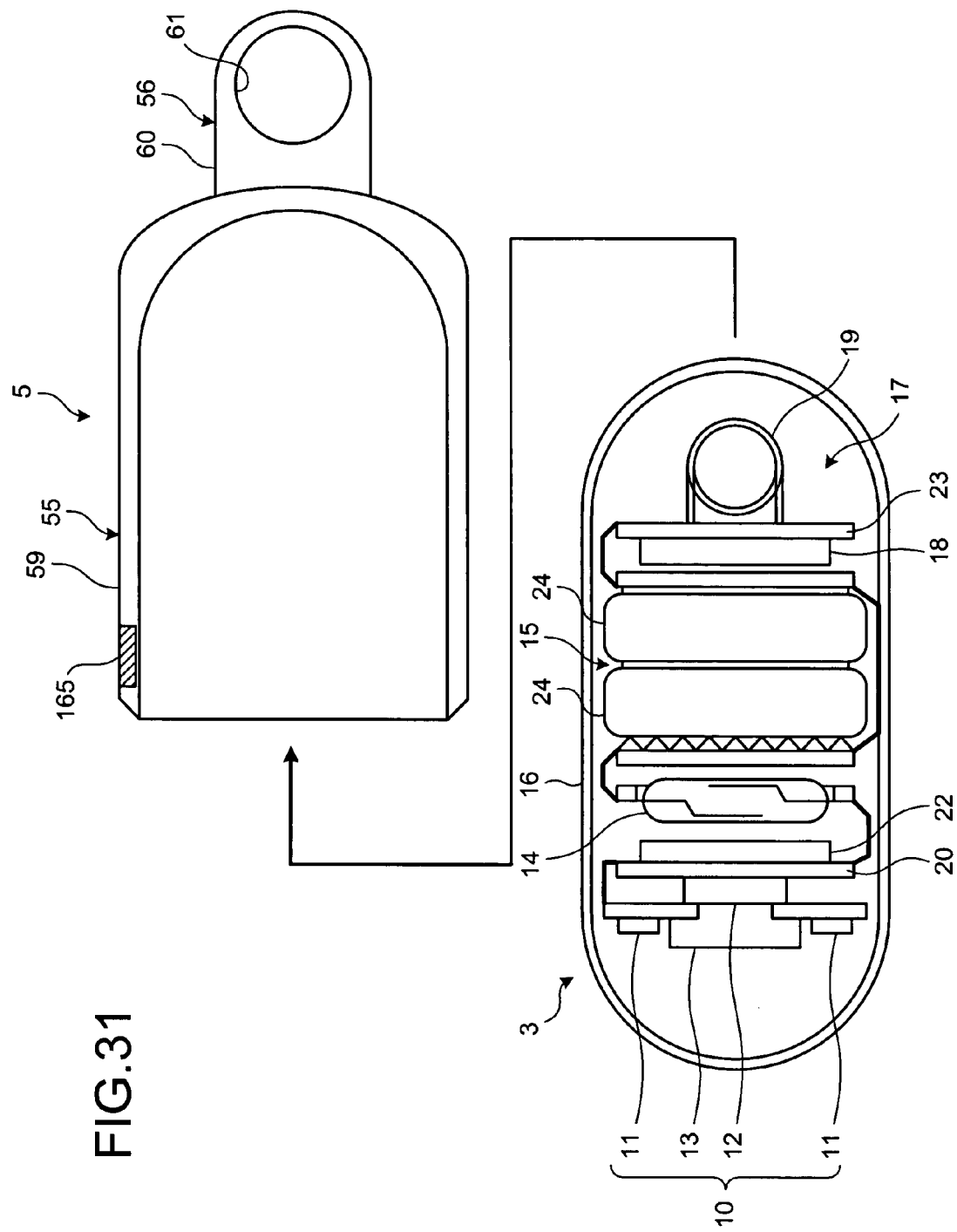
FIG. 31 is a cross sectional view showing an inner configuration of the body cavity introducing device placing system in which a capsule endoscope and an indwelling apparatus according to modification 2 of the seventh embodiment are separated.
Figure 32:
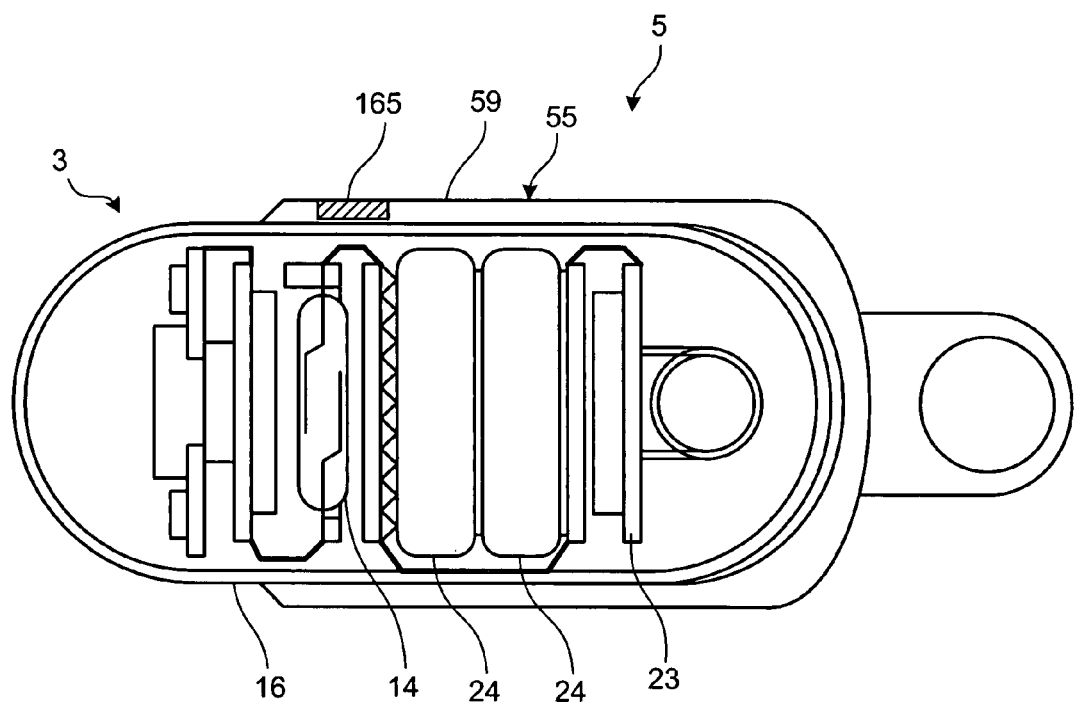
FIG. 32 is a cross sectional view showing an inner configuration of the body cavity introducing device placing system in which a capsule endoscope and an indwelling apparatus according to modification 2 are coupled.

FIG. 31 is a cross sectional view showing an inner configuration of the body cavity introducing device placing system in which the capsule endoscope and the indwelling apparatus according to modification 2 of the seventh embodiment are separated, and FIG. 32 is a cross sectional view showing an inner configuration of the body cavity introducing device placing system in which the capsule endoscope and the indwelling apparatus according to modification 2 are coupled. In modification 2, the switch between the normal mode and the placement mode is performed using a permanent magnet serving as a magnetic unit in place of the mechanical switch 128 of the first embodiment. That is, in modification 2, the permanent magnet 165 is arranged in the tube body 59 of the holding part 55 on the indwelling apparatus 5 side. The permanent magnet 165 is arranged at the position the reed switch serving as a magnetic detecting unit is ON/OFF controlled when the capsule endoscope 3 is accommodated in the tube body 59 of the holding part 55 in a holdable manner.

The reed switch 41 is turned ON when the permanent magnet 165 capable of generating a predetermined magnetic field is brought close and turned OFF when the permanent magnet 165 is moved away. In the normal mode of this modification, the permanent magnet 165 is brought close to the reed switch 14 and then moved away to be used. In other words, when the reed switch 14 is operated as OFF, ON, OFF, the system control circuit 27 determines the mode as the normal mode. The image sensor 10 and the RF transmission device 18 are operation controlled at a frame rate of every 0.5 seconds. In the placement mode, the capsule endoscope 3 is accommodated in the tube body 59 of the holding part 55 in a holdable manner, the permanent magnet 165 is brought close, and the relevant state is maintained for a constant time to be used. That is, when the reed switch 14 is operated from OFF and then turned ON and such state is maintained over a constant time, the system control circuit 27 determines the mode as the placement mode. The frame rate of imaging and transmission is switched to the placement mode of once every five minutes, and the image sensor 10 and the RF transmission device 18 are operation controlled.

Therefore, in modification 2, the ON/OFF state of the reed switch is changed by moving closer or moving away the permanent magnet with respect to the reed switch, the system control circuit recognizes the change and switches the frame rate of imaging and transmission from the normal mode of every 0.5 seconds to the placement mode of once every five minutes, and thus the power consumption in the capsule endoscope is reduced, and the battery drain of the capsule endoscope is reduced, similar to the first embodiment. Thus, in this embodiment, the photographing time interval is extended, and reduction of unnecessary image data and long time drive of the capsule endoscope are achieved.

In modification 2, the operation of the normal mode and the operation of the placement mode are switched by simply arranging the permanent magnet on the indwelling apparatus without adding the configuration of the capsule endoscope, and thus the operationality of the conventional capsule endoscope is enhanced.

The configuration of the reed switch may be such that the OFF state is obtained when magnetic field is applied and the contacting points contact, and the ON state is obtained when the electric field is not applied and the contacting points separate. In such configuration, the battery drain of the capsule endoscope is reduced, similar to the above modification, by moving the permanent magnet of the indwelling apparatus closer to the reed switch to apply the magnetic field and turn OFF the reed switch at the initial state, and operating the permanent magnet to move away from the reed switch so that the magnetic field is not applied and the reed switch is turned ON state when necessary. The reed switch performs the ON/OFF operation with a predetermined pattern, in which case, the effects similar to modification 1 are obtained by operating the permanent magnet according to the relevant pattern.

As another modification 3, a pressure sensor serving as a pressure detecting unit may be arranged on the capsule endoscope 3 in place of the mechanical switch, and the system control circuit may recognize the pressure applied to the capsule shaped housing when the capsule endoscope 3 is accommodated in the tube body 59 of the holding part 55 serving as a pressure unit in a holdable manner, in which case, effects similar to the first embodiment are also obtained.

Another modification 4 includes arranging a magnetic sensor serving as a magnetic detecting unit on the capsule shaped housing in place of the mechanical switch and arranging the permanent magnet serving as a magnetic unit on the indwelling apparatus, so that when the capsule endoscope 3 is accommodated in the tube body 59 of the holding part 55 in a holdable manner, the magnetic sensor detects the magnetism from the permanent magnet and the system control circuit recognizes the detected magnetism, in which case, the effects similar to the first embodiment are also obtained.

In The seventh embodiment, the frame rate in time of placement mode is once every five minutes, but the present invention is not limited thereto, and the imaging by means of the image sensor may be set at the imaging rate of every 0.5 seconds, and the transmission of data by means of the RF transmission device may be set at the transmission rate of once every five minutes. In this case, effects similar to the first embodiment are obtained, and recognition that the capsule endoscope is operating before the capsule is swallowed is facilitated since the LED is lighted at 0.5 second interval.

As modification 5, with regards to the placement mode, the imaging is not performed and only lighting of the LED is performed at interval of 0.5 second, and imaging and data transmission may be set at 5 minute interval. In this case, effects similar to the first embodiment are obtained, and recognition that the capsule endoscope is operating before the capsule is swallowed is facilitated since the LED is lighted at 0.5 second interval.

Furthermore, as modification 7, only beacon may be transmitted at an interval of 0.5 seconds and the like from the RF transmission device without performing imaging, which beacon may be received and checked at the in vitro receiving device, and data transmission may be performed with imaging performed at an interval of five minutes, in the case of the placement mode. In this case, the placement work is performed on the assumption that the receiving device has easily checked the operation of the capsule endoscope only with transmission and reception of the beacon without involving data transmission.

Moreover, as modification 7, assuming the capsule endoscope 3 and the in vitro device (receiving device 2) include first and second transmitting unit, and a wireless device serving as the first and second receiving units capable of performing transmission and reception, the image sensor may perform imaging and the data may be transmitted from the wireless device to the outside of the body only when a request for imaging is made from the in vitro device to the capsule endoscope. In this case, the treated location in the body cavity can be imaged only when the operator desires to check the image. Furthermore, circuits other than the receiving function of the wireless device may be in stand-by with the power turned OFF until a request for imaging is made, whereby the power (battery) is saved. In modification 6, the receiving device 2 constitutes the component of the body cavity introducing device placing system in addition to the capsule endoscope 3 and the indwelling apparatus 5.

The timing of acquiring the information of the inside of the body cavity is controlled by changing the rate of imaging and transmission of the image in the seventh embodiment, but the interval of imaging and transmission of the image can be changed and control the timing of controlling the timing of acquiring the information of the inside of the body cavity can be controlled when the system control circuit controls the timing of supplying power to the image sensor and the RF transmission device to change the time interval of turning ON and OFF the image sensor and the RF transmission device without changing the rate.

Eighth Embodiment

Figure 33:
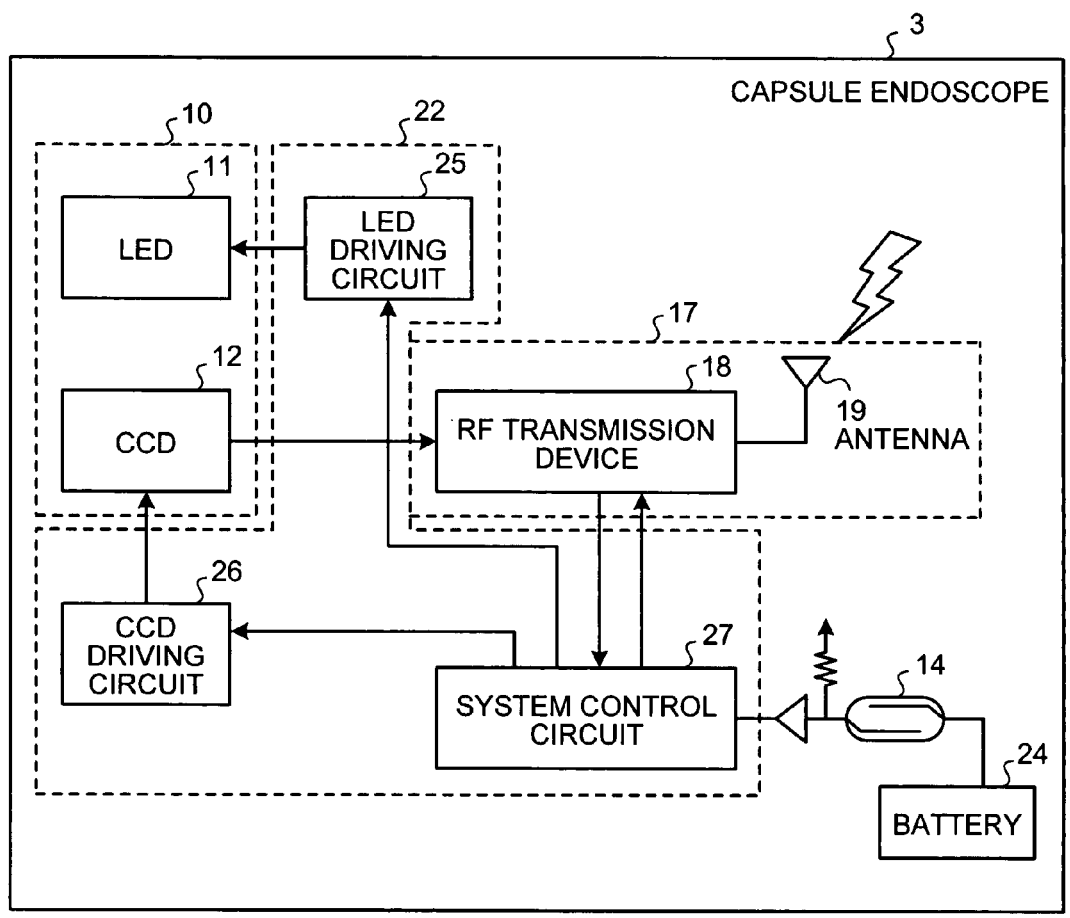
FIG. 33 is a block diagram showing a circuit configuration of a capsule endoscope according to the eighth embodiment shown in FIG. 1.

FIG. 33 is a block diagram showing a circuit configuration of the capsule endoscope according to an eighth embodiment shown in FIG. 1. The inner configuration of the capsule endoscope is similar to the configuration shown in FIG. 31, and thus the description thereof is not repeated. FIG. 33 differs from The seventh embodiment in that the capsule endoscope 3 is provided that indirectly determines the normal mode and the placement mode from the acquired information of the self-device without directly receiving the input of state control request from the outside such as pushing of button switch 128 by pin 157. In other words, the capsule endoscope 3 includes an LED 1 and a CCD 12 configuring the image sensor 10 serving as the information acquiring unit; includes the LED driving circuit 25 for controlling the driving state of the LED 11, the CCD driving circuit 26 for controlling the driving state of the CCD 12, and the system control circuit 27 for controlling the operation of the LED driving circuit 25, the CCD driving circuit 26 and the RF transmission device 18 serving as the communication unit as the signal processing and controlling unit 22; and includes the RF transmission device 18 and the antenna 19 as the wireless unit 17, where the image imaged with the CCD 12 is taken into the RF transmission device 18 having the image processing function serving as a brightness detecting unit to detect the brightness of the image, and the system control circuit 27 serving as the control unit determines the operation mode based on the detected brightness of the image.

Normally, when imaging the image, the image sensor 10 is operated simultaneously with the light emission of the LED 12 and the image is transmitted from the wireless unit 17 to the outside in the capsule endoscope. In this embodiment, the system control circuit 27 operation controls the image sensor 10 so as to perform data acquisition without light emitting the LED during imaging by the image sensor 10. The operation control is performed only at a constant time such as two minutes or 15 minutes after the power is turned ON.

If the image imaged within a constant time is brighter than a constant brightness (threshold value), the system control circuit 27 determines that the task by the endoscope is being performed in the subject 1, and switches the frame rate of imaging and transmission of the capsule endoscope 3 from the normal mode of every 0.5 seconds to the placement mode of once every five minutes. Furthermore, if the image imaged within the constant time is darker than the constant brightness, the system control circuit 27 determines that the normal observation is being performed and switches the frame rate of imaging and transmission of the capsule endoscope 3 to the normal mode of every 0.5. The image sensor 10 may be used for the sensor for checking the brightness of the inside of the body cavity, but a separate sensor may be arranged for detecting the brightness.

Therefore, in the eighth embodiment, if the brightness of the image taken by means of the image sensor that performs imaging of the image is brighter than the constant brightness, the operation mode is switched from the normal mode to the placement mode, and thus the power consumption in the capsule endoscope is reduced, and further, the battery drain of the capsule endoscope is reduced, similar to the seventh embodiment. Thus, in the present embodiment, the photographing time interval is extended, and reduction of unnecessary image data and long time drive of the capsule endoscope are possible.

As modification 1 of the eighth embodiment, a specific image pattern is imaged during a constant time after the power of the capsule endoscope 3 is turned ON, which image pattern is recognized by a pattern recognizing circuit serving as an image pattern detecting unit incorporated in the capsule endoscope and a mode change request is output to the system control circuit 27 to switch from the normal mode to the placement mode.

Therefore, in modification 1, the image pattern for mode switching is imaged with the capsule endoscope, and the operation mode is switched by performing the pattern recognition, and thus effects similar to the eighth embodiment are obtained.

As another modification 2, two or more generation patterns serving as a magnetic pattern of power ON are prepared in the external remote operation part (pattern generation circuit serving as a magnetic pattern generation unit and electromagnet) using the configuration disclosed in Japanese Patent Application Laid-Open No. 2005-73934 and the like. In the capsule endoscope, the magnetic sensor serving as the magnetic detecting unit detects the two generation patterns, and sets the two operation modes so as to allow power ON in the normal mode and the power ON in the placement mode in correspondence to the generated pattern. The system control circuit acquires the generation pattern, and the system control circuit switches and controls the operation mode to the normal mode or the placement mode.

Therefore, in modification 2, two generation patterns for operation are set, and the system control circuit switches the operation mode to the placement mode in correspondence to the placement generation pattern, and thus effects similar to the eighth embodiment are obtained.

Furthermore, in the eighth embodiment, power is supplied to the indwelling apparatus from the outside, and thus operation control of the capsule endoscope is performed from the outside, and versatility is enhanced. Moreover, in the eighth embodiment, the operation of the capsule endoscope adapted to the purpose for placement is realized with the control from the indwelling apparatus since the capsule endoscope is operated, as necessary.

In the embodiments 1 to 8, a case in which the image sensor acts the information acquiring unit is described by way of embodiment, but the present invention is not limited thereto, and pH sensor for measuring the pH of the inside of the body cavity, a temperature sensor for measuring the temperature of the inside of the body cavity, a pressure sensor for measuring the pressure of the inside of the body cavity, an enzyme sensor for detecting a specific protein of the inside of the body cavity, a blood sensor for detecting the blood of the inside of the body cavity and the like may be operation controlled as the information acquiring unit, similar to the image sensor.

Industrial Applicability

Therefore, the indwelling apparatus for body cavity introducing device and the body cavity introducing device placing system according to the present invention are useful for medical observation device, introduced inside the human body as the capsule endoscope, for observing the site to be examined, and is particularly suited for reducing the battery drain of the capsule endoscope.

Appended Claim

According to the above description, inventions of each claim provided in the following Appended claims and an arbitrary combination thereof are obtained.

(Appended claim 1) A body cavity introducing device comprising:
an information acquiring unit for acquiring body cavity information;
a transmitting unit for transmitting information acquired in the acquiring unit to an external device;
a request input unit for receiving an input of a state control request for changing the control state of the device; and
a control unit for controlling the operation state of at least one of the acquiring unit and the transmitting unit based on the input of the state control request by the request input unit.

(Appended claim 2) The body cavity introducing device according to Appended claim 1, wherein the request input unit is arranged on the exterior surface of the device.

(Appended claim 3) The body cavity introducing device according to Appended claim 1 or 2, wherein the request input unit comprises a switch unit that can be pushed serving as the state control request from the outside.

(Appended claim 4) The body cavity introducing device according to Appended claim 1 or 2, wherein the request input unit comprises a pressure detecting unit for detecting change in pressure serving as the state control request from the outside.

(Appended claim 5) The body cavity introducing device according to Appended claim 1 or 2, wherein the request input unit comprises a magnetism detecting unit for detecting change in magnetism serving as the state control request from the outside.

(Appended claim 6) The body cavity introducing device according to Appended claim 1 or 2, wherein the request input unit comprises a potential detecting unit for detecting change in potential serving as the state control request from the outside.

(Appended claim 7) The body cavity introducing device according to Appended claim 1 or 2, wherein the request input unit comprises a receiving unit for receiving a wireless signal serving as the state control request from the outside.

(Appended claim 8) The body cavity introducing device according to Appended claim 1 or 2, wherein the request input unit comprises a brightness detecting unit for detecting brightness of the body cavity information serving as the state control request acquired within a predetermined time by the information acquiring unit.

(Appended claim 9) The body cavity introducing device according to Appended claim 1 or 2, wherein the request input unit comprises an image pattern detecting unit for detecting a specific image pattern serving as the state control request acquired by the information acquiring unit.

(Appended claim 10) The body cavity introducing device according to Appended claim 1 or 2, wherein the request input unit comprises a magnetic generation pattern detecting unit for detecting a magnetic generation pattern serving as the state control request from the outside.

(Appended claim 11) The body cavity introducing device according to Appended claim 1, wherein the information acquiring unit comprises an image sensor including an illumination unit for illuminating the inside of the body cavity, an imaging unit for imaging the inside of the body cavity illuminated by the illumination unit, and an optical unit for imaging an image of the inside of the body cavity onto the imaging unit.

(Appended claim 12) The body cavity introducing device according to Appended claim 1, wherein the information acquiring unit comprises a pH sensor for measuring the pH of the inside of the body cavity.

(Appended claim 13) The body cavity introducing device according to Appended claim 1, wherein the information acquiring unit comprises a temperature sensor for measuring the temperature of the inside of the body cavity.

(Appended claim 14) The body cavity introducing device according to Appended claim 1, wherein the information acquiring unit comprises a pressure sensor for measuring the pressure of the inside of the body cavity.

(Appended claim 15) The body cavity introducing device according to Appended claim 1, wherein the information acquiring unit comprises an enzyme sensor for measuring a specific protein of the inside of the body cavity.

(Appended claim 16) The body cavity introducing device according to Appended claim 1, wherein the information acquiring unit comprises a blood sensor for measuring blood of the inside of the body cavity.

(Appended claim 17) The body cavity introducing device according to Appended claim 1, wherein the body cavity introducing device comprises a capsule endoscope.

(Appended claim 18) An in vivo information acquiring device comprising:
an in vivo information acquiring device main body;
an operation mode switching request switch, arranged in the in vivo information acquiring device main body, for receiving an operation mode switching request from outside the in vivo information acquiring device main body; and
a control section for changing the operation state in the in vivo information acquiring device main body from a first operation mode of receiving the switching request to a second operation mode which is an operation state different from the first operation mode when the operation mode switching request switch receives the switching request.

(Appended claim 19) An in vivo information acquiring device placing system comprising:
an in vivo information acquiring device main body including an operation mode switching request switch with a plurality of operation modes and a control section for changing the operation state in the in vivo information acquiring device main body from a first operation mode prior to receiving the switching request to a second operation mode which is an operation state different from the first operation mode when the operation mode switching request switch receives the switching request; and
an indwelling apparatus including an attachment for attaching the in vivo information acquiring device main body, an operation mode switching request unit for issuing the operation mode switching request to the operation mode switching request switch when the in vivo information acquiring device main body is attached to the attachment, and a hook part for hooking to the inside of the living body.

(Appended claim 20) An indwelling apparatus for in vivo information acquiring device comprising:
an attachment for attaching the in vivo information acquiring device main body;
an operation mode switching request unit for issuing the operation mode switching request to the in vivo information acquiring device main body attached to the attachment; and
a hook part for hooking to the inside of the living body.

(Appended claim 21) A body cavity introducing device placing system comprising:
a body cavity introducing device including an information acquiring unit for acquiring body cavity information, a transmitting unit for transmitting information acquired in the acquiring unit to an external device, a request input unit for receiving an input of a state control request for changing the control state of the device, and a control unit for controlling the operation state of at least one of the acquiring unit and the transmitting unit based on the input of the state control request by the request input unit; and an indwelling apparatus for body cavity introducing device including a(holding unit for holding the body cavity introducing device for acquiring information on the body cavity, and a body cavity tissue binding unit for fixing to the tissue of the body cavity.

(Appended claim 22) The body cavity introducing device placing system according to Appended claim 21, wherein the indwelling apparatus for body cavity introducing device further includes a request output unit for outputting the state control request.

(Appended claim 23) The body cavity introducing device placing system according to Appended claim 21, wherein the request input unit comprises a switch unit that can be pushed serving as the state control request from the outside; and the request output unit comprises a pushing unit for pushing the switch unit when the holding unit is holding the body cavity introducing device.

(Appended claim 24) The body cavity introducing device placing system according to Appended claim 21, wherein the request input unit comprises a pressure detecting unit for detecting change in pressure serving as the state control request from the outside; and the request output unit comprises a pressure unit for applying pressure to the outer surface of the body cavity introducing device when the holding unit is holding the body cavity introducing device.

(Appended claim 25) The body cavity introducing device placing system according to Appended claim 21, wherein the request input unit comprises a magnetic detecting unit for detecting change in magnetism serving as the state control request from the outside; and the request output unit comprises a magnetic unit for applying magnetism to the body cavity introducing device when the holding unit is holding the body cavity introducing device.

(Appended claim 26) The body cavity introducing device placing system according to Appended claim 21, wherein the request input unit comprises a potential detecting unit for detecting change in potential serving as the state control request from the outside; and the request output unit comprises a potential unit for applying a predetermined potential to the body cavity introducing device when the holding unit is holding the body cavity introducing device.

(Appended claim 27) The body cavity introducing device placing system according to Appended claim 21, the request input unit comprises a magnetic pattern detecting unit for detecting a magnetic pattern serving as the state control request from the outside; and the request output unit comprises a magnetic pattern generation unit for outputting the predetermined magnetic pattern to the body cavity introducing device when the holding unit is holding the body cavity introducing device.

(Appended claim 28) A body cavity introducing device placing system comprising:

a body cavity introducing device including an information acquiring unit for acquiring body cavity information, a first transmitting unit for transmitting information acquired at the acquiring unit to an external device, a first receiving unit serving as a request input unit for receiving an input of a state control request for changing the control state of the device, and a control unit for controlling the operation state of at least one of the acquiring unit and the transmitting unit based on the input of the state control request by the first receiving unit;

an indwelling apparatus for body cavity introducing device including a holding unit for holding the body cavity introducing device for acquiring the information of the inside of the body cavity, and a body cavity tissue binding unit for fixing to the tissue of the inside of the body cavity; and an external device including a second receiving unit for receiving the information transmitted from the transmitting unit, and a second transmitting unit for transmitting a wireless signal serving as the state control request based on the information received at the receiving unit.

The invention claimed is:

1. A body cavity introducing device placing system comprising:
    a capsule endoscope for acquiring information of the inside of a body cavity, the capsule endoscope having a capsule endoscope body; and
    an indwelling apparatus comprising:
        a holding unit for coupling the capsule endoscope body to the indwelling apparatus;
        a binding unit configured to fix the coupled capsule endoscope body and indwelling apparatus to tissue in the body cavity; and
        a capsule endoscope control unit for controlling a power consuming operation of the capsule endoscope;
        wherein the holding unit comprises a holding part formed of a tube body for coupling the capsule endoscope body to the indwelling apparatus, an inner diameter of the holding part being substantially the same as an outer diameter of the capsule endoscope body,
        the capsule endoscope control unit comprises a first interface, which is disposed at one end of the tube body for receiving an input from an external device, and a second interface for transmitting a signal for controlling the power consuming operation of the capsule endoscope to the capsule endoscope, the second interface comprising an output unit for outputting the signal to the capsule endoscope, and
        the output unit is disposed on the tube body,
    wherein the coupled indwelling apparatus and capsule endoscope body is configured to be swallowed entirely so as to be capable of traversing the digestive system of the subject; and
    the capsule endoscope control unit controls a power switch of the capsule endoscope, the power switch being arranged at substantially the same position as the output unit when the capsule endoscope is held by the holding part.

2. A capsule endoscope placing system, comprising:
    a capsule endoscope including,
        a capsule endoscope body;
        an information acquiring unit disposed in the capsule endoscope body for acquiring information of the inside of the body cavity,
        a transmitting unit disposed in the capsule endoscope body for transmitting the information acquired in the information acquiring unit to an external device,
        an internal control unit disposed in the capsule endoscope body for controlling the information acquiring unit and the transmitting unit,
        a power supplying unit disposed in the capsule endoscope body for supplying power to each of the units,
        a power switch disposed in the capsule endoscope body for controlling the power supply from the power supplying unit to each of the units; and
    an indwelling apparatus for the capsule endoscope including,
        a holding unit for coupling the capsule endoscope body to the indwelling apparatus, a body cavity tissue binding unit configured to fix the coupled capsule endoscope body and indwelling apparatus to tissue in the body cavity, and a capsule endoscope control unit for controlling power consuming operation of the capsule endoscope;

wherein the holding unit comprises a holding part formed of a tube body for coupling the capsule endoscope body to the indwelling apparatus, an inner diameter of the holding part being substantially the same as a largest outer diameter of the capsule endoscope body, the capsule endoscope control unit comprises a first interface, which is disposed at one end of the tube body for receiving an input from the external device, and a second interface for transmitting a signal for controlling the power consuming operation of the capsule endoscope to the capsule endoscope, the second interface comprising an output unit for outputting the signal to the capsule endoscope, the output unit is disposed on the tube body, the capsule endoscope control unit controls the power switch of the capsule endoscope, the power switch being arranged at substantially the same position as the output unit when the capsule endoscope is held by the holding part, and the coupled indwelling apparatus and capsule endoscope body is configured to be swallowed entirely so as to be capable of traversing the digestive system of the subject.

3. A body cavity introducing device placing system, comprising:

a body cavity introducing device including,
  an information acquiring unit for acquiring information of the inside of the body cavity,
  a transmitting unit for transmitting the information acquired in the information acquiring unit to an external device,
  an internal control unit for controlling the information acquiring unit and the transmitting unit,
  a power supplying unit for supplying power to each of the units,
  a power switch for switching the power supply from the power supplying unit to each of the units; and an indwelling apparatus for the body cavity introducing device including,
  a holding unit for holding the body cavity introducing device, a body cavity tissue binding unit for fixing to the tissue in the body cavity,
  a body cavity introducing device control unit for controlling turning on and off of the power switch, and
  a switch for activating the body cavity introducing device control unit, wherein the switch is turned on in a state where the body cavity introducing device is held by the indwelling apparatus, and the body cavity introducing device is introduced into a body cavity in a state where the body cavity introducing device control unit controls turning on and off of the power switch; and wherein the switch comprises an optical sensor, the body cavity introducing device control unit comprises an LED, the power switch is controlled to be turned on and off by detection of light of the LED with the optical sensor, after the power switch is turned on, the optical sensor detects illumination intensity, and the rate of transmission of the information by the transmitting unit is set fast when the illumination intensity is higher than a certain level, whereas the rate of transmission is set slow when the illumination intensity is lower than the certain level.

4. The body cavity introducing device placing system according to claim 3, wherein the body cavity introducing device control unit issues an operation start command and an operation stop command to the body cavity introducing device attached to the holding unit.

5. The indwelling apparatus for body cavity introducing device according to claim 3, wherein the body cavity introducing control unit issues the operation start command and the operation stop command upon receiving a wireless signal.

6. The indwelling apparatus for body cavity introducing device according to claim 3, wherein the body cavity introducing device control unit repeatedly outputs the operation start command and the operation stop command at a predetermined time interval.

* * * * *